(12) United States Patent
Maienfisch et al.

(10) Patent No.: US 8,524,896 B2
(45) Date of Patent: Sep. 3, 2013

(54) CHEMICAL COMPOUNDS

(75) Inventors: Peter Maienfisch, Stein (CH); Ottmar Hueter, Stein (CH); Peter Renold, Stein (CH); Werner Zambach, Stein (CH); Thomas Pitterna, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 190 days.

(21) Appl. No.: 12/921,000

(22) PCT Filed: Mar. 2, 2009

(86) PCT No.: PCT/EP2009/052435
§ 371 (c)(1),
(2), (4) Date: Sep. 3, 2010

(87) PCT Pub. No.: WO2009/109539
PCT Pub. Date: Sep. 11, 2009

(65) Prior Publication Data
US 2011/0009261 A1    Jan. 13, 2011

(30) Foreign Application Priority Data
Mar. 4, 2008 (GB) .................................. 0804067.7

(51) Int. Cl.
| | | |
|---|---|---|
| *C07D 293/10* | (2006.01) | |
| *C07D 251/00* | (2006.01) | |
| *C07D 253/00* | (2006.01) | |
| *C07D 237/02* | (2006.01) | |
| *C07D 211/78* | (2006.01) | |
| *C07D 213/63* | (2006.01) | |
| *A01N 25/26* | (2006.01) | |
| *A01N 43/54* | (2006.01) | |
| *A01N 41/12* | (2006.01) | |
| *A61K 31/53* | (2006.01) | |
| *A61K 31/501* | (2006.01) | |
| *A61K 31/435* | (2006.01) | |

(52) U.S. Cl.
USPC .............. 544/1; 544/480; 544/219; 544/224; 544/239; 544/242; 544/336; 546/1; 546/286; 546/288; 546/290; 546/292; 546/330; 546/331; 504/100; 504/189; 504/209; 504/309; 504/312; 504/326; 504/350; 514/222.5; 514/241; 514/247; 514/252.05; 514/256; 514/277

(58) Field of Classification Search
USPC ............ 544/1, 180, 219, 224, 239, 242, 336; 546/1, 286, 288, 290, 292, 293, 294, 300, 546/301, 302, 330, 331; 504/100, 189, 209, 504/309, 312, 326, 350
See application file for complete search history.

(56) References Cited

U.S. PATENT DOCUMENTS

2007/0111985 A1    5/2007  Naidu et al.
2008/0207447 A1*   8/2008  Kaiser et al. ................. 504/100

FOREIGN PATENT DOCUMENTS

| EP | 0033984 | 8/1981 |
|---|---|---|
| WO | 2007014913 | 2/2007 |
| WO | 2007060220 | 5/2007 |

* cited by examiner

*Primary Examiner* — Jane C Oswecki
(74) *Attorney, Agent, or Firm* — Brian D. McAlhaney

(57) ABSTRACT

A compound of the formula (I) where, for example, W, X and Y are each CH; $R^1$ and $R^6$ together with the adjacent nitrogen forms a 3 to 10-membered saturated ring, wherein the ring may contain, in addition to the nitrogen and carbon ring members, 1, 2 or 3 heteroatoms and/or heteroatom groups as ring members, independently of one another, selected from the group consisting of sulfur, CO, SO, $SO_2$ and N—$R^7$ and/or the ring may carry 1, 2 or 3 radicals, independently of one another, each selected, for example, from the group consisting of halogen, cyano, nitro, amino, and C1-C6-alkyl. $R^2$ is, for example, halogen, C1-C6-alkyl, C1-C6-haloalkyl, C1-C6-alkoxy, C1-C6-haloalkoxy or C1-C6-alkoxy-C1-C6-alkoxy, and $R^7$ is for example, $R^{10}C(=O)$, C1-C6 alkyl or C1-C6-haloalkyl; and/or salts thereof; and their use as pesticidal agents.

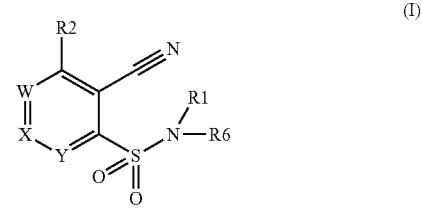

(I)

16 Claims, No Drawings

CHEMICAL COMPOUNDS

This application is a 371 of International Application No. PCT/EP2009/052435 filed Mar. 2, 2009, which claims priority to GB 0804067.7 filed Mar. 4, 2008, the contents of which are incorporated herein by reference.

The present invention relates to certain ortho-substituted cyano(hetero)aryl sulfonyl compounds, and salts thereof, compositions and treated material thereof, and method of using such compounds and salts.

EP 33984, WO2005035486, WO2006056433, WO2006100271, WO2006100288, WO2007060220, WO2007014913 disclose cyanobenzene or cyanopyridine derivatives having pesticidal activity.

It has now been found that certain cyano(hetero)aryl sulfonyl compounds have pesticidal properties. The present invention, in a first aspect, accordingly relates to a compound of the formula I

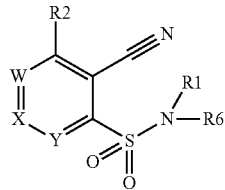

where

W is N, NO, or C—$R^3$;
X is N, NO or C—$R^4$;
Y is N, NO, or C—$R^6$;
$R^1$ and $R^6$ together with the adjacent nitrogen forms a 3 to 10-membered saturated ring, wherein the ring may contain, in addition to the nitrogen and carbon ring members, 1, 2 or 3 heteroatoms and/or heteroatom groups as ring members, independently of one another, selected from the group consisting of oxygen, sulfur, CO, SO, $SO_2$ and N—$R^7$ and/or the ring may carry 1, 2 or 3 radicals, independently of one another, each selected from the group consisting of halogen, cyano, nitro, amino, C1-C6-alkyl, C1-C6-haloalkyl, C1-C6-alkoxy and C1-C6-haloalkoxy,
$R^2$ is H, halogen, cyano, C1-C6-alkyl, C1-C6-haloalkyl, C1-C6-alkoxy, C1-C6-haloalkoxy, C1-C6-alkylthio, C1-C6-alkylsulfinyl, C1-C6-alkylsulfonyl, C1-C6-haloalkylthio, C1-C6-haloalkylsulfinyl, C1-C6-haloalkylsulfonyl, C2-C6-alkenyl, C2-C6-alkynyl, C2-C6-haloalkenyl, C2-C6-haloalkynyl, amino, (C1-C6-alkyl)amino, di(C1-C6-alkyl)amino, aminosulfonyl, aminosulfinyl, aminosulfenyl, or $R^9C(=O)$; provided that the C1-C6-alkyl, C1-C6-haloalkyl, C1-C6-alkoxy, C1-C6-haloalkoxy, C1-C6-alkylthio, C1-C6-alkylsulfinyl, C1-C6-alkylsulfonyl, C1-C6-haloalkylthio, C1-C6-haloalkylsulfinyl, C1-C6-haloalkylsulfonyl, C2-C6-alkenyl, C2-C6-alkynyl, C2-C6-haloalkenyl, C2-C6-haloalkynyl, (C1-C6-alkyl)amino, di(C1-C6-alkyl)amino radicals may be unsubstituted, or may carry 1, 2 or 3 radicals, independently of one another, each selected from the group consisting of cyano, nitro, amino, OH, C1-C6-alkyl, C1-C6-haloalkyl, C1-C6-alkoxy, C1-C6-alkylthio, C1-C6-alkylsulfinyl, C1-C6-alkylsulfonyl, C1-C6-haloalkoxy, C1-C6-haloalkylthio, (C1-C6-alkoxy)carbonyl, (C1-C6-alkyl)amino, di(C1-C6-alkyl)amino, C3-C8-cycloalkyl and partially or fully unsaturated ring system; and provided that the $R^9C(=O)$ radical may be unsubstituted, or when $R^9$ is C1-C6-alkoxy, (C1-C6-alkyl)amino, di(C1-C6-alkyl)amino, aryl, aryl-C1-C6-alkyl and C1-C6-alkyl, the alkyl moiety may carry one or more halogen atoms, or
$R^9$ is 5- to 6-membered heteroaryl, wherein the heteroaryl ring contains as ring members 1, 2 or 3 heteroatoms and/or heteroatom groups, independently of one another, selected from the group consisting of nitrogen, oxygen, sulfur, SO, $SO_2$ and N—R″, wherein R″ is hydrogen or C1-C6-alkyl, or
$R^9$ is 3- to 7-membered heterocyclyl, wherein the heterocyclic ring is saturated or partly unsaturated and contains 1, 2 or 3 heteroatoms and/or heteroatom groups, independently of one another, selected from the group consisting of nitrogen, oxygen, sulfur, group SO, $SO_2$ and N—$R^8$, wherein $R^8$ is hydrogen or C1-C6-alkyl, and wherein the carbon atoms of the heterocyclic rings may be unsubstituted or substituted by 1 or 2 radicals, independently of one another, selected from halogen and C1-C6-alkyl.
$R^3$, $R^4$ and $R^5$, independently of each other, are H, halogen, cyano, azido, nitro, C1-C6-alkyl, C3-C8-cycloalkyl, C1-C6-haloalkyl, C1-C6-alkoxy, C1-C6-haloalkoxy, C1-C6-alkylthio, C1-C6-alkylsulfinyl, C1-C6-alkylsulfonyl, C1-C6-haloalkylthio, C2-C6-alkenyl, C2-C6-alkynyl, C2-C6-haloalkenyl, C2-C6-haloalkynyl, amino, (C1-C6-alkyl)amino, di(C1-C6-alkyl)amino, aminosulfonyl, aminosulfinyl, aminosulfenyl, $R^9C(=O)$, aryl or heteroaryl, which heteroaryl may contain 1, 2 or 3 heteroatoms as ring members, independently of one another, selected from the group consisting of nitrogen, oxygen and sulfur and/or which aryl or heteroaryl may carry 1, 2 or 3 substituents, independently of one another, selected from the group consisting of halogen, C1-C6-alkyl, C1-C6-haloalkyl, C1-C6-alkoxy and C1-C6-haloalkoxy;
provided that if one of W, X or Y is not N, $R^1$ and $R^6$ together with the adjacent nitrogen form a 3 to 10-membered saturated ring, wherein the ring may contain, in addition to the nitrogen and carbon ring members, 1, 2 or 3 heteroatoms and/or heteroatom groups as ring members, independently of one another, selected from the group consisting of oxygen, sulfur, CO, SO, $SO_2$ and N—$R^7$ and/or the ring may carry 1, 2 or 3 radicals, independently of one another, each selected from the group consisting of halogen, cyano, nitro, amino, C1-C6-alkyl, C1-C6-haloalkyl, C1-C6-alkoxy and C1-C6-haloalkoxy;
$R^7$ is hydrogen, $R^{10}C(=O)$, C1-C6 alkyl or C1-C6-haloalkyl;
each $R^9$ independently is selected from the group consisting of hydrogen, hydroxyl, C1-C6-alkoxy, amino, (C1-C6-alkyl)amino, di(C1-C6-alkyl)amino, aryl, aryl-C1-C6-alkyl and C1-C6-alkyl, where the alkyl moiety in the two last-mentioned radicals and the aryl moiety in aryl or aryl-C1-C6-alkyl may carry one or more halogen atoms,
5- to 6-membered heteroaryl, wherein the heteroaryl ring contains as ring members 1, 2 or 3 heteroatoms and/or heteroatom groups, independently of one another, selected from the group consisting of nitrogen, oxygen, sulfur, SO, $SO_2$ and N—R″, wherein R″ is hydrogen or C1-C6-alkyl, and
3- to 7-membered heterocyclyl, wherein the heterocyclic ring is saturated or partly unsaturated and contains 1, 2 or 3 heteroatoms and/or heteroatom groups, independently of one another, selected from the group consisting of nitrogen, oxygen, sulfur, group SO, $SO_2$ and N—$R^8$ wherein $R^8$ is hydrogen or C1-C6-alkyl, and wherein the carbon atoms of the heterocyclic rings may be unsubstituted or substituted by 1 or 2 radicals, independently of one another, selected from halogen and C1-C6-alkyl; and each $R^{10}$ independently is H, C1-C6-alkyl or C1-C6-haloalkyl;
and/or salts thereof.

The compounds of formula (I) may exist in different geometric or optical isomers or tautomeric forms. This invention covers all such isomers and tautomers and mixtures thereof in all proportions. In particular, in the case compounds of the formula I have one or more centers of chirality, they can be present as mixtures of enantiomers or diastereomers. The present invention provides both the pure enantiomers or diastereomers or mixtures of each thereof, as well as isotopic forms such as deuterated compounds.

The organic moieties mentioned in the above definitions of the variables are collective terms for individual listings of the individual group members. The prefix Cn-Cm indicates in each case the possible number of carbon atoms in the group. Similarly the terms "x to y membered" indicates the possible number of atoms forming a closed chain in the corresponding ring.

The term halogen denotes in each case fluorine, bromine, chlorine or iodine.

The phrase "may carry one or more halogen atoms" refers to one or more of the radicals carrying one or more halogen atoms; in the case of two or more halogen atoms, the atoms can be different, preferably the halogen atoms are the same. Accordingly, one carbon atom can also carry up to three halogen atoms, depending on its position and substitution degree in said radical.

The term "C1-C6-alkyl" as used herein refers to a saturated straight-chain or branched hydrocarbon radical attached via any of the carbon atoms having 1 to 6 carbon atoms, for example, any one of the radicals 1-methylbutyl, 2-methylbutyl, 3-methylbutyl, 2,2-dimethylpropyl, 1-ethylpropyl, n-hexyl, n-pentyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "C1-C6-haloalkyl" as used herein refers to a straight-chain or branched saturated alkyl radical attached via any of the carbon atoms having 1 to 6 carbon atoms (as mentioned above), where some or all of the hydrogen atoms in these radicals may be replaced by fluorine, chlorine, bromine and/or iodine, i.e., for example, any one of chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl. According a term "C1-C2-fluoroalkyl" would refer to a C1-C2-alkyl radical which carries 1,2, 3,4, or 5 fluorine atoms, for example, any one of difluoromethyl, trifluoromethyl, 1-fluoroethyl, 2-fluoroethyl, 2,2-difluoroethyl, 2,2,2-trifluoroethyl, 1,1,2,2-tetrafluoroethyl or penta-fluoroethyl.

The term "C1-C6-alkoxy" as used herein refers to a straight-chain or branched saturated alkyl radical having 1 to 6 carbon atoms (as mentioned above) which is attached via an oxygen atom, i.e., for example, any one of methoxy, ethoxy, n-propoxy, 1-methylethoxy, n-butoxy, 1-methylpropoxy, 2-methylpropoxy or 1,1-dimethylethoxy. Similarly, the terms "alkenoxy", "alkynoxy" and "benzyloxy" refers to the corresponding alkenyl, alkynyl and benzyl radical respectively which is attached via an oxygen atom.

The term "C1-C6-haloalkoxy" as used herein refers to a C1-C6-alkoxy radical as mentioned above which is partially or fully substituted by fluorine, chlorine, bromine and/or iodine, i.e., for example, any one of chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroeth-oxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy.

The term "(C3-C8-cyloalkyl)thio" as used herein refers to a monocyclic hydrocarbon radical having 3 to 8 carbon atoms which is attached via a sulfur atom, for example, 2-cyclopentylthio, 2-cyclopentylthio or 3-cyclobutylthio. Such radicals are also being referred to as (C—C8-cyloalkyl)sulfanyl.

The term "C1-C6-alkylthio" (or C1-C6-alkylsulfanyl: C1-C6-alkyl-S—) as used herein refers to a straight chain or branched saturated alkyl radical having 1 to 6 carbon atoms (as mentioned above) which is attached via a sulfur atom, i.e., for example, any one of methylthio, ethylthio, n-propylthio, 1-methylethylthio, butylthio, 1-methylpropylthio, 2-methylpropylthio or 1,1-dimethylethylthio.

The term "C1-C6-alkylsulfinyl" (or C1-C6-alkyl-S(=O)—) as used herein refers to a straight chain or branched saturated alkyl radical having 1 to 6 carbon atoms (as mentioned above) which is attached via the sulfur atom of the sulfinyl group, i.e., for example, any one of CH3-SO, C2H5-SO, n-propylsulfinyl, 1-methylethyl-sulfinyl, n-butylsulfinyl, 1-methylpropylsulfinyl, 2-methylpropylsulfinyl, 1,1-dimethyl-ethylsulfinyl, n-pentylsulfinyl, 1-methylbutylsulfinyl, 2-methylbutylsulfinyl, 3-methyl-butylsulfinyl, 1,1-dimethylpropylsulfinyl, 1,2-dimethylpropylsulfinyl, 2,2-dimethylpropylsulfinyl or 1-ethylpropylsulfinyl.

The term "C1-C6-alkylsulfonyl" (or C1-C6-alkyl-S(=O)$_2$—) as used herein refers to a straight chain or branched saturated alkyl radical having 1 to 6 carbon atoms (as mentioned above) which is attached via the sulfur atom of the sulfonyl group, i.e., for example, any one of CH3-S02, C2H5-S02, n-propylsulfonyl, (CH3)2CH—S02, n-butylsulfonyl, 1-methylpropylsulfonyl, 2-methylpropylsulfonyl or (CH3)3C—S02. The term "C1-C6-haloalkylthio" as used herein refers to a C1-C6-alkylthio radical as mentioned above which is partially or fully substituted by fluorine, chlorine, bromine and/or iodine, i.e., for example, any one of fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio or nonafluorobutylthio.

The term "C1-C6-alkoxycarbonyl" as used herein refers to a straight chain or branched alkoxy radical having 1 to 6 carbon atoms (as mentioned above) which is attached via the carbon atom of the carbonyl group, i.e., for, any one of methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl or 1,1-dimethylethoxycarbonyl.

The term "C2-C6-alkenyl" as used herein refers to a straight chain or branched mono-unsaturated hydrocarbon radical attached via any of the carbon atoms having 2 to 6 carbon atoms and a double bond in any position, i.e., for example, any one of ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl.

The term "C2-C6-alkynyl" as used herein refers to a straight chain or branched aliphatic hydrocarbon radical attached via any of the carbon atoms which contains a C—C triple bond and has 2 to 6 carbons atoms: for example, any one of ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "C3-C8-cycloalkyl" as used herein refers to a monocyclic hydrocarbon radical having 3 to 8 carbon atoms, for example, any one of cyclopropyl, cyclobutyl, cyclopentyl, cyclo-hexyl, cycloheptyl or cyclooctyl.

The term "(C1-C6-alkyl)amino" as used herein refers to a straight chain or branched saturated alkyl radical having 1 to 6 carbon atoms (as mentioned above) which is attached via the nitrogen atom of the amino group, i.e., for example, any one of methylamino, ethylamino, n-propylamino, 1-methylethylamino, n-butylamino, 1-methylpropylamino, 2-methylpropylamino or 1,2-dimethylethylamino.

The term "di(C1-C6-alkyl)amino" as used herein refers to two straight chain or branched saturated alkyl radicals having 1 to 6 carbon atoms (as mentioned above), each of which is attached via the nitrogen atom of the amino group, for example, any one of N,N-dimethylamino, N,N-diethylamino, N,N-di(1-methylethyl)amino, N,N-dipropylamino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)-amino, N-methyl-N-(2-methypropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethyl-ethyl)amino, N-(1-methylethyl)-N-propylamino, N-butyl-N-propylamino, N-(1-methyl-propyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)-amino, N-(1-methylethyl)-N-(2-methylpropyl)amino, N-(1,1-dimethylethyl)-N-(1-methyl-ethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)-amino.

The term "ring" as used herein refers to a radical or substituent having a group of atoms forming a closed chain, the ring may be saturated, or partially or fully unsaturated. The ring may contain only carbon atoms or may contain carbon atoms and one or more heteroatoms selected from the group consisting of oxygen, sulfur and nitrogen atoms. Examples are cycloalkyl, saturated or partially saturated heterocyclyl, aryl, heteroaryl.

The term "ring system" as used herein refers to a radical or substituent having one or more rings, each ring may, independently of each other, be saturated, or partially or fully unsaturated, and/or the one or more rings in the ring system may contain within the closed chain one or more heteroatoms and/or heteroatom groups and/or the ring may be substituted. The ring may be bound (or attached) directly to the remainder of the compound or be bound (or attached) via a linking group, such as C1-C6-alkylene, which may be unsubstituted, substituted with halogen and/or C1-C6-alkyl, and/or the linking group may contain at least one hetero atom and/or heteroatom group selected from N, O, S, SO, $SO_2$, and C(=O). In the case of two or more rings, two rings may be fused together, bridged (such as norborane), spiro connected, or connected by a bridging group (e.g. C1-C2-alkylene), an atom (such as sulfur or oxygen) or a bond. In the case of partially or fully unsaturated ring system, the degree of unsaturation refers to the whole ring system rather than of a single ring in the ring system. The ring system contains only carbon atoms in the ring(s), or contains in at least one ring 1, 2, 3 heteroatoms and/or heteroatom groups as ring members, independently of one another, selected from the group consisting of nitrogen, oxygen, C(=O) and sulfur. In an embodiment, a ring in the partially or fully unsaturated ring system is unsubstituted, or may carry one or more halogen atoms and/or may carry 1, 2 or 3 substituents, independently of the rings (in the instance of two or more rings) and substituents, selected from the group consisting of C1-C6-alkyl, C1-C6-haloalkyl, C1-C6-alkoxy and C1-C6-haloalkoxy. In an embodiment, the ring system is partially or fully unsaturated ring system. In a preferred embodiment, the partially or fully unsaturated ring system is a 5 or 6-membered monocyclic ring system or a 9 or 10-membered bicyclic ring system. Examples of ring systems include aryl, phenyl, benzyl, cyclopropyl, heterocyclic, heteroaryl, heteroaryl-C1-C6-alkyl, naphthyl, 4-methoxy-benzyl, furan-2-yl-methyl, thiophen-2-yl-methyl, pyridin-4-yl-methyl, 1-(4-methoxy-phenyl)-ethyl, 1-(furan-2-yl)-ethyl, 1-(thiophen-2-yl)-ethyl, 1-(pyridin-4-yl)-ethyl, triazole-1-yl-propyl, 6-methoxy-1,2,3,4-tetrahydro-naphtalen-1-yl, biphenyl, spiro-[4,4]-bicyclononyl, bicyclo-[2,2,1-]hepanyl, 7-oxa-bicyclo-[2,2,1-]hepanyl, tropanyl, and 6-dimethyl-4,5,6,7-tetrahydro-benzofuran-4-yl.

The term "heterocyclyl" as used herein (and also in heterocyclyl-C1-C6-alkyl) refers to a saturated or partially unsaturated non-aromatic cyclic radical having one or more rings, preferably having in each ring 3 to 7 ring members, wherein 1, 2 or 3 ring members of the cyclic radical are heteroatoms independently selected from O, N and S, and/or heteroatom groups independently selected from S=O, S(O)2 and N—R with R being H or C1-C6-alkyl. In the case of two or more rings, the rings may be fused together or connected by a bridging group or atom. Examples for non-aromatic rings include azetidiyl, pyrrolidinyl, pyrazolinyl, imidazolinyl, pyrrolinyl, pyrazolinyl, imidazolinyl, tetrahydrofuranyl, dihydrofuranyl, 1,3-dioxolanyl, dioxolenyl, thiolanyl, dihydrothienyl, oxazolidinyl, isoxazol idinyl, oxazolinyl, isoxazolinyl, thiazolinyl, isothiazolinyl, thiazolidinyl, isothiazolidinyl, oxathiolanyl, piperidinyl, piperazinyl, pyranyl, dihydropyranyl, tetrahydropyranyl, dioxanyl, thiopyranyl, dihydrothiopyranyl, tetrahydrothiopyranyl, morpholinyl, thiazinyl and the like.

The term "aryl" (and also in aryl-C1-C6-alkyl) as used herein refers to an aromatic hydrocarbon ring, which may be mono-, bi- or tricyclic. Examples of such rings include phenyl, naphthalenyl, anthracenyl, indenyl or phenanthrenyl. A preferred aryl group is phenyl The term "heteroaryl" as used herein (and also in "heteroaryl-C1-C6-alkyl") refers to an aromatic cyclic radical having one or more rings, preferably having in each ring 3 to 7 ring members, more preferably in each ring 5 or 6 ring members ("C5-C6-heteroaryl" or "5- or 6-membered heteroaryl"), wherein 1, 2, 3 or 4 ring members of the cyclic radical are heteroatoms independently selected from O, N and S and/or heteroatom groups independently selected from S=O, S(O)$_2$ and N—R, with R being H or alkyl. Examples for monocyclic 5- or 6-membered heteroaromatic rings include triazinyl, pyrazinyl, pyrimidyl, pyridazinyl, pyridyl, thienyl, furyl, pyrrolyl, pyrazolyl, imidazolyl, triazolyl, tetrazolyl, thiazolyl, oxazolyl, thiadiazolyl, oxadiazolyl, isothiazolyl and isoxazolyl.

The term "aryl-C1-C6-alkyl" as used herein (and also C3-C8-cycloalkyl-C1-C6-alkyl, heteroaryl-C1-C6-alkyl, heterocyclic-C1-C6-alkyl) refers to the respective radical being bound to the remainder of the molecule via any carbon atoms of the C1-C6-alkylene group. Examples of "aryl-C1-C6-alkyl" are benzyl, 1-phenylethyl and 2-phenylethyl. Similarly, for aryl-C2-C6-alkenyl and aryl-C2-C6-alkynyl refers to the aryl radical being bound to the remainder of the molecule via any carbon atoms of the C2-C6-alkenylene and C2-C6 alkynylene group respectively.

The term "ethylenically unsaturated ring" as used herein means that the ring contains at least one double bond which may be a C—C double bond but also a double bond containing at least one heteroatom, e.g. C=N or N=N.

In a preferred embodiment, the C1-C6-moiety, whenever it is indicated, for example, as a C1-C6-alkyl substituent or radical, C1-C6-alkoxy, C1-C6-haloalkoxy, C1-C6-alkylthio, C1-C6-alkylsulfonyl, C1-C6-alkylsulfinyl, C1-C6-haloalkylthio, C1-C6-haloalkyl, (C1-C6-alkyl)amino, di(C1-C6-alkyl)amino, etc, is, independent of the type of moiety, a C1-C4-moiety, preferably a C1-C3-moiety, for example, any one of a C1-moiety, a C2-moiety or a C3-moiety. If there are more than one alkyl moities, the chain length may differ.

In a preferred embodiment, the C2-C6-moiety, whenever it is indicated, for example, as a C2-C6-alkenyl substituent or radical, C2-C6-alkynyl, C2-C6-haloalkenyl, C2-C6-haloalkynyl, C2-C6-alkenyoxy, C2-C6-alkenyloxy, C2-C6-alkynyloxy, etc, is, independent of the type of moiety, a C2-C5-moiety, preferably a C2-C4-moiety, for example, any one of a C2-moiety, a C3-moiety or a C4-moiety.

In a preferred embodiment, the C3-C8-moiety, whenever it is indicated, for example, as a C3-C8-cycloalkyl substituent or radical, C3-C8-cyclohaloalkyl, C3-C8-cycloalkoxy, etc, is, independent of the type of moiety, a C3-C5-moiety, for example, any one of a C3-moiety, or a C5-moiety.

In an embodiment, independent of the other embodiments, W, X, Y are each C—$R^3$, C—$R^4$, C—$R^6$ respectively, preferably each CH.

In an embodiment, independent of the other embodiments, W, X and Y are each C—$R^3$, C—$R^4$ and C—$R^6$ respectively, $R^1$ and $R^6$ together with the adjacent nitrogen forms a 3 to 10-membered saturated ring, wherein the ring may contain, in addition to the nitrogen and carbon ring members, 1, 2 or 3 heteroatoms and/or heteroatom groups as ring members, independently of one another, selected from the group consisting of oxygen, sulfur, CO, SO, SO$_2$ and N—$R^7$ and/or the ring may carry 1, 2 or 3 radicals, independently of one another, each selected from the group consisting of halogen, cyano, nitro, amino, C1-C6-alkyl, C1-C6-haloalkyl, C1-C6-alkoxy and C1-C6-haloalkoxy; and $R^7$ is as defined above.

In an embodiment, independent of the other embodiments,
W is N, NO, or C—$R^3$;
X is N, NO or C—$R^4$;
Y is N, NO, or C—$R^6$;
$R^1$ and $R^6$ together with the adjacent nitrogen forms a 3 to 10-membered saturated ring, wherein the ring may contain, in addition to the nitrogen and carbon ring members, 1, 2 or 3 heteroatoms and/or heteroatom groups as ring members, independently of one another, selected from the group consisting of sulfur, CO, SO, SO$_2$ and N—$R^7$ and/or the ring may carry 1, 2 or 3 radicals, independently of one another, each selected from the group consisting of halogen, cyano, nitro, amino, C1-C6-alkyl, C1-C6-haloalkyl, C1-C6-alkoxy and C1-C6-haloalkoxy; and $R^7$ is as defined above.

In an embodiment, independent of the other embodiments, W and Y is CH and X is CH or N In an embodiment, independent of the other embodiments, at least one of W, X and Y is N or NO. Preferably either W and Y is, independent of each other, N or NO and X is CR$^4$, or each of W, X and Y are each N.

In an embodiment, independent of other embodiments, W and Y are C—$R^3$ and C—$R^5$ respectively, and X is N or NO, then $R^1$ and $R^6$ together with the adjacent nitrogen forms a 3 to 10-membered saturated ring, wherein the ring may contain, in addition to the nitrogen and carbon ring members, 1, 2 or 3 heteroatoms and/or heteroatom groups as ring members, independently of one another, selected from the group consisting of sulfur, CO, SO, $SO_2$ and N—$R^7$ and/or the ring may carry 1, 2 or 3 radicals, independently of one another, each selected from the group consisting of halogen, cyano, nitro, amino, C1-C6-alkyl, C1-C6-haloalkyl, C1-C6-alkoxy and C1-C6-haloalkoxy.

In an embodiment, at least one W, X and Y is not N or NO, and in such an event the $R^1$ and $R^6$ together with the adjacent nitrogen forms a 3 to 10-membered saturated ring, wherein the ring may contain, in addition to the nitrogen and carbon ring members, 1, 2 or 3 heteroatoms and/or heteroatom groups as ring members, independently of one another, selected from the group consisting of oxygen, sulfur, CO, SO, $SO_2$ and N—$R^7$ and/or the ring may carry 1, 2 or 3 radicals, independently of one another, each selected from the group consisting of halogen, cyano, nitro, amino, C1-C6-alkyl, C1-C6-haloalkyl, C1-C6-alkoxy and C1-C6-haloalkoxy. Preferably at least one W, X and Y is N or NO, and then $R^1$ and $R^6$ together with the adjacent nitrogen forms a 3 to 10-membered saturated ring, wherein the ring may contain, in addition to the nitrogen and carbon ring members, 1, 2 or 3 heteroatoms and/or heteroatom groups as ring members, independently of one another, selected from the group consisting of sulfur, CO, SO, $SO_2$ and N—$R^7$ and/or the ring may carry 1, 2 or 3 radicals, independently of one another, each selected from the group consisting of halogen, cyano, nitro, amino, C1-C6-alkyl, C1-C6-haloalkyl, C1-C6-alkoxy and C1-C6-haloalkoxy.

In an embodiment, independent of other embodiments, $R^2$ is halogen, C1-C6-alkyl, C1-C6-haloalkyl, C1-C6-alkoxy, C1-C6-haloalkoxy or C1-C6-alkoxy-C1-C6-alkoxy. In a preferred embodiment, $R^2$ is halogen, C1-C6-alkyl, C1-C6-haloalkyl, C1-C6-alkoxy or C1-C6-haloalkoxy.

In an embodiment the 3 to 10-membered ring is a 5, 6, or 7-membered ring. Suitable examples are 1,7 Naphthridinyl; Morpholinyl; Thiomorpholinyl; 1,7-Naphthydridinyl; 2,7-Naphthydridinyl; Pyrazino[2,1-c][1,4]oxazin-3(4H)-onyl; 2-Oxa-5-azabicyclo[2.2.1]heptanyl; 2-Thia-5-azabicyclo[2.2.1]heptanyl; 2,5-Diazabicyclo[2.2.1]heptanyl; piperazinyl; 2-Morpholinonyl; Thiazolidinyl; 2H-Pyrido[1,2-a]pyrazinyl; Hexahydro-1H-azepinyl; Hexahydro-1H-thiazepinyl; Decahydro-quinoxalinyl; Hexahydro-1,4-oxazepinyl; Hexahydro-1,4-diazepinyl; 1,4-Diazabicyclo[3.2.1]octan-2-onyl; 1,3-Diazabicyclo[3.2.2]nonanyl; 1,4-Diazabicyclo[3.2.1]octanyl; 1-piperazinonyl; Hexahydro-1H-1,4-diazepinyl; Hexahydro-1,4-oxazepinyl; 2-piperazinonyl; Octahydro-furo[3,4-b]pyridinyl; Octahydro-furo[3,4-c]pyridinyl; Octahydro-pyrrolo[3,4-c]pyrrolyl; Octahydro-pyrrolo[1,2-a]pyrimidinyl; Tetrahydro-1,3,5-triazin-2(1H)-onyl; Octahydro-1,5-diazocinyl; Hexahydro-2H-1,5-thiazocinyl; Hexahydro-2H-1,5-oxazocinyl; Tetrahydro-2H-1,3-thiazinyl; Tetrahydro-2H-1,3-oxazinyl; 5-Oxazolidinonyl; 5-Isoxazolindinonyl; 5-Isoxazolidinyl; Hexahydro-pyridazinyl; Tetrahydro-2H-1,2-oxazinyl; Pyrazolidinyl; 3-Pyrazolidinonyl; Tetrahydro-1,3,4-oxadiazinyl; Tetrahydro-1,2-oxazin-6-onyl; Diaziridinyl; 4-Piperidinonyl; 3-Piperidinonyl; 3-Pyrrolidinonyl; Hexahydro-3H-azepin-3-onyl; and Hexahydro-4H-azepin-4-only.

In an embodiment particularly preferred compounds of formula I are where W, X and Y are each CH.

In an embodiment, preferred compounds formula I are where W and X and are each CH; and Y is haloC1 (e.g. CF).

In an embodiment, preferred compounds formula I are where W and Y are each CH; and X is N, then $R^1$ and $R^6$ together with the adjacent nitrogen forms a 3 to 10-membered saturated ring, wherein the ring may contain, in addition to the nitrogen and carbon ring members, 1, 2 or 3 heteroatoms and/or heteroatom groups as ring members, independently of one another, selected from the group consisting of sulfur, CO, SO, $SO_2$ and N—$R^7$ and/or the ring may carry 1, 2 or 3 radicals, independently of one another, each selected from the group consisting of halogen, cyano, nitro, amino, C1-C6-alkyl, C1-C6-haloalkyl, C1-C6-alkoxy and C1-C6-haloalkoxy.

In an embodiment, independent of other embodiments, wherein W, X and Y are each CH, $R^2$ is selected from halogen, C1-C6-alkyl, C1-C6-haloalkyl, C1-C6-alkoxy and C1-C6-haloalkoxy, and $R^1$ and $R^6$ together with the adjacent nitrogen forms a 3 to 10-membered saturated ring, wherein the ring may contain, in addition to the nitrogen and carbon ring members, 1, 2 or 3 heteroatoms and/or heteroatom groups as ring members, independently of one another, selected from the group consisting of oxygen, sulfur, CO, SO, $SO_2$ and N—$R^7$ and/or the ring may carry 1, 2 or 3 radicals, independently of one another, each selected from the group consisting of halogen, cyano, nitro, amino, C1-C6-alkyl, C1-C6-haloalkyl, C1-C6-alkoxy and C1-C6-haloalkoxy; and $R^7$ is as defined above.

In an embodiment, independent of other embodiments, wherein W and Y are each CH, X is N, $R^2$ is selected from halogen, C1-C6-alkyl, C1-C6-haloalkyl, C1-C6-alkoxy and C1-C6-haloalkoxy, and $R^1$ and $R^6$ together with the adjacent nitrogen forms a 3 to 10-membered saturated ring, wherein the ring may contain, in addition to the nitrogen and carbon ring members, 1, 2 or 3 heteroatoms and/or heteroatom groups as ring members, independently of one another, selected from the group consisting of sulfur, CO, SO, $SO_2$ and N—$R^7$ and/or the ring may carry 1, 2 or 3 radicals, independently of one another, each selected from the group consisting of halogen, cyano, nitro, amino, C1-C6-alkyl, C1-C6-haloalkyl, C1-C6-alkoxy and C1-C6-haloalkoxy; and $R^7$ is as defined above.

In an embodiment, independent of other embodiments, wherein W and Y are each CH, X is N, $R^2$ is C1-C6-alkoxy, and $R^1$ and $R^6$ together with the adjacent nitrogen forms a 3 to 10-membered saturated ring, wherein the ring may contain, in addition to the nitrogen and carbon ring members, 1, 2 or 3 heteroatoms and/or heteroatom groups as ring members, independently of one another, selected from the group consisting of sulfur, CO, SO, $SO_2$ and N—$R^7$ and/or the ring may carry 1, 2 or 3 radicals, independently of one another, each selected from the group consisting of halogen, cyano, nitro, amino, C1-C6-alkyl, C1-C6-haloalkyl, C1-C6-alkoxy and C1-C6-haloalkoxy; and $R^7$ is as defined above.

In an embodiment, independent of other embodiments, wherein $R^1$ and $R^6$ together with the adjacent nitrogen forms a 3 to 10-membered ring, wherein the ring contains, in addition to the nitrogen and carbon ring members, a sulfur atom, or a group selected from CO, SO, and $SO_2$ and the ring may carry 1, 2 or 3 radicals, independently of one another, each selected from the group consisting of halogen, cyano, nitro, amino, C1-C6-alkyl, C1-C6-haloalkyl, C1-C6-alkoxy and C1-C6-haloalkoxy. In a preferred embodiment, $R^1$ and $R^6$ together with the adjacent nitrogen form a 5 membered ring containing, in addition to the nitrogen and carbon ring members, a sulfur atom or a group selected from CO, SO, and $SO_2$. In an especially preferred embodiment, $R^1$ and $R^6$ together with the adjacent nitrogen is thiazolidinyl.

Particularly preferred compounds of formula I are where W, X and Y are each CH; $R^2$ is selected from halogen, C1-C6- alkyl, C1-C6-haloalkyl, C1-C6-alkoxy, C1-C6-haloalkoxy or C1-C6-alkoxy-C1-C6-alkoxy; and $R^1$ and $R^6$ is selected from 1,7 Naphthridinyl; Morpholinyl; Thiomorpholinyl; 1,7-Naphthydridinyl; 2,7-Naphthydridinyl; Pyrazino[2,1-c][1,4]oxazin-3(4H)-onyl; 2-Oxa-5-azabicyclo[2.2.1]heptanyl; 2-Thia-5-azabicyclo[2.2.1]heptanyl; 2,5-Diazabicyclo[2.2.1]heptanyl; piperazinyl; 2-Morpholinonyl; Thiazolidinyl; 2H-Pyrido[1,2-a]pyrazinyl; Hexahydro-1H-azepinyl; Hexahydro-1H-thiazepinyl; Decahydro-quinoxalinyl; Hexahydro-1,4-oxazepinyl; Hexahydro-1,4-diazepinyl; 1,4-Diazabicyclo[3.2.1]octan-2-onyl; 1,3-Diazabicyclo[3.2.2]nonanyl; 1,4-Diazabicyclo[3.2.1]octanyl; 1-piperazinonyl; Hexahydro-1H-1,4-diazepinyl; Hexahydro-1,4-oxazepinyl; 2-piperazinonyl; Octahydro-furo[3,4-b]pyridinyl; Octahydro-furo[3,4-c]pyridinyl; Octahydro-pyrrolo[3,4-c]pyrrolyl; Octahydro-pyrrolo[1,2-a]pyrimidinyl; Tetrahydro-1,3,5-triazin-2(1H)-onyl; Octahydro-1,5-diazocinyl; Hexahydro-2H-1,5-thiazocinyl; Hexahydro-2H-1,5-oxazocinyl; Tetrahydro-2H-1,3-thiazinyl; Tetrahydro-2H-1,3-oxazinyl; 5-Oxazolidinonyl; 5-Isoxazolindinonyl; 5-Isoxazolidinyl; Hexahydro-pyridazinyl; Tetrahydro-2H-1,2-oxazinyl; Pyrazolidinyl; 3-Pyrazolidinonyl; Tetrahydro-1,3,4-oxadiazinyl; Tetrahydro-1,2-oxazin-6-onyl; Diaziridinyl; 4-Piperidinonyl; 3-Piperidinonyl; 3-Pyrrolidinonyl; Hexahydro-3H-azepin-3-onyl; and Hexahydro-4H-azepin-4-only.

In an embodiment, preferred compounds of formula I are where W and X and are each CH; Y is haloC1 (e.g. CF); $R^2$ is selected from halogen, C1-C6-alkyl, C1-C6-haloalkyl, C1-C6-alkoxy, C1-C6-haloalkoxy or C1-C6-alkoxy-C1-C6-alkyl; and $R^1$ and $R^6$ is selected from 1,7 Naphthridinyl; Morpholinyl; Thiomorpholinyl; 1,7-Naphthydridinyl; 2,7-Naphthydridinyl; Pyrazino[2,1-c][1,4]oxazin-3(4H)-onyl; 2-Oxa-5-azabicyclo[2.2.1]heptanyl; 2-Thia-5-azabicyclo[2.2.1]heptanyl; 2,5-Diazabicyclo[2.2.1]heptanyl; piperazinyl; 2-Morpholinonyl; Thiazolidinyl; 2H-Pyrido[1,2-a]pyrazinyl; Hexahydro-1H-azepinyl; Hexahydro-1H-thiazepinyl; Decahydro-quinoxalinyl; Hexahydro-1,4-oxazepinyl; Hexahydro-1,4-diazepinyl; 1,4-Diazabicyclo[3.2.1]octan-2-onyl; 1,3-Diazabicyclo[3.2.2]nonanyl; 1,4-Diazabicyclo[3.2.1]octanyl; 1-piperazinonyl; Hexahydro-1H-1,4-diazepinyl; Hexahydro-1,4-oxazepinyl; 2-piperazinonyl; Octahydro-furo[3,4-b]pyridinyl; Octahydro-furo[3,4-c]pyridinyl; Octahydro-pyrrolo[3,4-c]pyrrolyl; Octahydro-pyrrolo[1,2-a]pyrimidinyl; Tetrahydro-1,3,5-triazin-2(1H)-onyl; Octahydro-1,5-diazocinyl; Hexahydro-2H-1,5-thiazocinyl; Hexahydro-2H-1,5-oxazocinyl; Tetrahydro-2H-1,3-thiazinyl; Tetrahydro-2H-1,3-oxazinyl; 5-Oxazolidinonyl; 5-Isoxazolindinonyl; 5-Isoxazolidinyl; Hexahydro-pyridazinyl; Tetrahydro-2H-1,2-oxazinyl; Pyrazolidinyl; 3-Pyrazolidinonyl; Tetrahydro-1,3,4-oxadiazinyl; Tetrahydro-1,2-oxazin-6-onyl; Diaziridinyl; 4-Piperidinonyl; 3-Piperidinonyl; 3-Pyrrolidinonyl; Hexahydro-3H-azepin-3-onyl; and Hexahydro-4H-azepin-4-only.

In an embodiment, preferred compounds of formula I are where W and Y and are each CH; X is N; $R^2$ is selected from halogen, C1-C6-alkyl, C1-C6-haloalkyl, C1-C6-alkoxy, C1-C6-haloalkoxy or C1-C6-alkoxy-C1-C6-alkyl; and $R^1$ and $R^6$ is selected from Morpholinyl; Thiomorpholinyl; piperazinyl; 2-Morpholinonyl; Thiazolidinyl; Hexahydro-1H-azepinyl; Hexahydro-1H-thiazepinyl; Hexahydro-1,4-oxazepinyl; Hexahydro-1,4-diazepinyl; 1-piperazinonyl; Hexahydro-1H-1,4-diazepinyl; Hexahydro-1,4-oxazepinyl; 2-piperazinonyl; Tetrahydro-2H-1,3-thiazinyl; Tetrahydro-2H-1,3-oxazinyl; 5-Oxazolidinonyl; 5-Isoxazolindinonyl; 5-Isoxazolidinyl; Hexahydro-pyridazinyl; Tetrahydro-2H-1,2-oxazinyl; Pyrazolidinyl; 3-Pyrazolidinonyl; Tetrahydro-1,3,4-oxadiazinyl; Tetrahydro-1,2-oxazin-6-onyl; Diaziridinyl; 4-Piperidinonyl; 3-Piperidinonyl; 3-Pyrrolidinonyl; Hexahydro-3H-azepin-3-onyl; and Hexahydro-4H-azepin-4-only.

In the event $R^2$ is fluorine, a preferred embodiment of compound of formula I is W and Y are each CH, and $R^1$ and $R^6$ together with the adjacent nitrogen forms a 3 to 10-membered saturated ring, wherein the ring may contain, in addition to the nitrogen and carbon ring members, 1, 2 or 3 heteroatoms and/or heteroatom groups as ring members, independently of one another, selected from the group consisting of sulfur, CO, $SO_2$ and N—$R^7$ and/or the ring may carry 1, 2 or 3 radicals, independently of one another, each selected from the group consisting of halogen, cyano, nitro, amino, C1-C6-alkyl, C1-C6-haloalkyl, C1-C6-alkoxy and C1-C6-haloalkoxy.

Specific examples of formula I are disclosed in the Tables below.

Table 1.1: A compound of formula (I), wherein $R^2$ is methyl, W is C—H, X is C—H, Y is C—H, and the values for $R^1$ and $R^6$ are as given in the Table A.

Table 1.2: A compound of formula (I), wherein $R^2$ is ethyl, W is C—H, X is C—H, Y is C—H, and the values for $R^1$ and $R^6$ are as given in the Table A Table 1.3: A compound of formula (I), wherein $R^2$ is trifluoromethyl, W is C—H, X is C—H, Y is C—H, and the values for $R^1$ and $R^6$ are as given in the Table A Table 1.4: A compound of formula (I), wherein $R^2$ is trichloromethyl, W is C—H, X is C—H, Y is C—H, and the values for $R^1$ and $R^6$ are as given in the Table A Table 1.5: A compound of formula (I), wherein $R^2$ is fluoro, W is C—H, X is C—H, Y is C—H, and the values for $R^1$ and $R^6$ are as given in the Table A Table 1.6: A compound of formula (I), wherein $R^2$ is chloro, W is C—H, X is C—H, Y is C—H, and the values for $R^1$ and $R^6$ are as given in the Table A Table 1.7: A compound of formula (I), wherein $R^2$ is iodo, W is C—H, X is C—H, Y is C—H, and the values for $R^1$ and $R^6$ are as given in the Table A Table 1.8: A compound of formula (I), wherein $R^2$ is bromo, W is C—H, X is C—H, Y is C—H, and the values for $R^1$ and $R^6$ are as given in the Table A Table 1.9: A compound of formula (I), wherein $R^2$ is methoxy, W is C—H, X is C—H, Y is C—H, and the values for $R^1$ and $R^6$ are as given in the Table A Table 1.10: A compound of formula (I), wherein $R^2$ is trifluoromethoxy, W is C—H, X is C—H, Y is C—H, and the values for $R^1$ and $R^6$ are as given in the Table A Table 1.11: A compound of formula (I), wherein $R^2$ is trichloromethoxy, W is C—H, X is C—H, Y is C—H, and the values for $R^1$ and $R^6$ are as given in the Table A Table 1.12: A compound of formula (I), wherein $R^2$ is difluoromethoxy, W is C—H, X is C—H, Y is C—H, and the values for $R^1$ and $R^6$ are as given in the Table A Table 1.13: A compound of formula (I), wherein $R^2$ is difluorochloromethoxy, W is C—H, X is C—H, Y is C—H, and the values for $R^1$ and $R^6$ are as given in the Table A Table 1.14: A compound of formula (I), wherein $R^2$ is monofluoromethoxy, W is C—H, X is C—H, Y is C—H, and the values for $R^1$ and $R^6$ are as given in the Table A Table 1.15: A compound of formula (I), wherein $R^2$ is dichlorormethoxy, W is C—H, X is C—H, Y is C—H, and the values for $R^1$ and $R^6$ are as given in the Table A Table 1.16: A compound of formula (I), wherein $R^2$ is monochlororomethoxy, W is C—H, X is C—H, Y is C—H, and the values for $R^1$ and $R^6$ are as given in the Table A Table 1.17: A compound of formula (I), wherein $R^2$ is $OCH_2$—$OCH_3$, W is C—H, X is C—H, Y is C—H, and the values for $R^1$ and $R^6$ are as given in the Table A Table 1.18: A compound of formula (I), wherein $R^2$ is ethoxy, W is C—H, X is C—H, Y is C—H, and the values for $R^1$ and $R^6$ are as given in the Table A Table 1.19: A compound of formula (I), wherein $R^2$ is difluorochloromethyl, W is C—H, X is C—H, Y is C—H, and the values for $R^1$ and $R^6$ are as given in the Table A Table 1.20: A compound of formula (I), wherein $R^2$ is difluoromethyl, W is C—H, X is C—H, Y is C—H, and the values for $R^1$ and $R^6$ are as given in the Table A Table 1.21: A compound of formula (I), wherein $R^2$ is methyl, W is C—H, X is C—H, Y is C—F, and the values for $R^1$ and $R^6$ are as given in the Table A Table 1.22: A compound of formula (I), wherein $R^2$ is ethyl, W is C—H, X is C—H, Y is C—F, and the values for $R^1$ and $R^6$ are as given in the Table A Table 1.23: A compound of formula (I), wherein $R^2$ is trifluoromethyl, W is C—H, X is C—H, Y is C—F, and the values for $R^1$ and $R^6$ are as given in the Table A Table 1.24: A compound of formula (I), wherein $R^2$ is trichloromethyl, W is C—H, X is C—H, Y is C—F, and the values for $R^1$ and $R^6$ are as given in the Table A Table 1.25: A compound of formula (I), wherein $R^2$ is fluoro, W is C—H, X is C—H, Y is C—F, and the values for $R^1$ and $R^6$ are as given in the Table A Table 1.26: A compound of formula (I), wherein $R^2$ is chloro, W is C—H, X is C—H, Y is C—F, and the values for $R^1$ and $R^6$ are as given in the Table A Table 1.27: A compound of formula (I), wherein $R^2$ is bromo, W is C—H, X is C—H, Y is C—F, and the values for $R^1$ and $R^6$ are as given in the Table A Table 1.28: A compound of formula (I), wherein $R^2$ is iodo, W is C—H, X is C—H, Y is C—F, and the values for $R^1$ and $R^6$ are as given in the Table A Table 1.29: A compound of formula (I), wherein $R^2$ is methoxy, W is C—H, X is C—H, Y is C—F, and the values for $R^1$ and $R^6$ are as given in the Table A Table 1.30: A compound of formula (I), wherein $R^2$ is trifluoromethoxy, W is C—H, X is C—H, Y is C—F, and the values for $R^1$ and $R^6$ are as given in the Table A Table 1.31: A compound of formula (I), wherein $R^2$ is trichloromethoxy, W is C—H, X is C—H, Y is C—F, and the values for $R^1$ and $R^6$ are as given in the Table A Table 1.32: A compound of formula (I), wherein $R^2$ is difluoromethoxy, W is C—H, X is C—H, Y is C—F, and the values for $R^1$ and $R^6$ are as given in the Table A Table 1.33: A compound of formula (I), wherein $R^2$ is difluorochloromethoxy, W is C—H, X is C—H, Y is C—F, and the values for $R^1$ and $R^6$ are as given in the Table A Table 1.34: A compound of formula (I), wherein $R^2$ is dichloromethoxy, W is C—H, X is C—H, Y is C—F, and the values for $R^1$ and $R^6$ are as given in the Table A Table 1.35: A compound of formula (I), wherein $R^2$ is monochloromethoxy, W is C—H, X is C—H, Y is C—F, and the values for $R^1$ and $R^6$ are as given in the Table A Table 1.36: A compound of formula (I), wherein $R_2$ is ethoxy, W is C—H, X is C—H, Y is C—F, and the values for $R^1$ and $R^6$ are as given in the Table A Table 1.37: A compound of formula (I), wherein $R^2$ is $OCH_2$—$OCH_3$, W is C—H, X is C—H, Y is C—F, and the values for $R^1$ and $R^6$ are as given in the Table A Table 1.38: A compound of formula (I), wherein $R^2$ is monofluoromethoxy, W is C—H, X is C—H, Y is C—F, and the values for $R^1$ and $R^6$ are as given in the Table A Table 1.39: A compound of formula (I), wherein $R^2$ is difluorochloromethyl, W is C—H, X is C—H, Y is C—F, and the values for $R^1$ and $R^6$ are as given in the Table A Table 1.40: A compound of formula (I), wherein $R^2$ is difluoromethyl, W is C—H, X is C—H, Y is C—F, and the values for $R^1$ and $R^6$ are as given in the Table A Table 1.41: A compound of formula (I), wherein $R^2$ is methyl, W is C—H, X is N, Y is C—H, and the values for $R^1$ and $R^6$ are as given in the Table B Table 1.42: A compound of formula (I), wherein $R^2$ is ethyl, W is C—H, X is N, Y is C—H, and the values for $R^1$ and $R^6$ are as given in the Table B Table 1.43: A compound of formula (I), wherein $R^2$ is trifluoromethyl, W is C—H, X is N, Y is C—H, and the values for $R^1$ and $R^6$ are as given in the Table B Table 1.44: A compound of formula (I), wherein $R^2$ is trichloromethyl, W is C—H, X is N, Y is C—H, and the values for $R^1$ and $R^6$ are as given in the Table B Table 1.45: A compound of formula (I), wherein $R^2$ is fluoro, W is C—H, X is N, Y is C—H, and the values for $R^1$ and $R^6$ are as given in the Table B Table 1.46: A compound of formula (I), wherein $R^2$ is chloro, W is C—H, X is N, Y is C—H, and the values for $R^1$ and $R^6$ are as given in the Table B Table 1.47: A compound of formula (I), wherein $R^2$ is bromo, W is C—H, X is N, Y is C—H, and the values for $R^1$ and $R^6$ are as given in the Table B Table 1.48: A compound of formula (I), wherein $R^2$ is iodo, W is C—H, X is N, Y is C—H, and the values for $R^1$ and $R^6$ are as given in the Table B Table 1.49: A compound of formula (I), wherein $R^2$ is methoxy, W is C—H, X is N, Y is C—H, and the values for $R^1$ and $R^6$ are as given in the Table B Table 1.50: A compound of formula (I), wherein $R^2$ is trifluoromethoxy, W is C—H, X is N, Y is C—H, and the values for $R^1$ and $R^6$ are as given in the Table B Table 1.51: A compound of formula (I), wherein $R^2$ is trichloromethoxy, W is C—H, X is N, Y is C—H, and the values for $R^1$ and $R^6$ are as given in the Table B Table 1.52: A compound of formula (I), wherein $R^2$ is difluormethoxy, W is C—H, X is N, Y is C—H, and the values for $R^1$ and $R^6$ are as given in the Table B Table 1.53: A compound of formula (I), wherein $R^2$ is monofluormethoxy, W is C—H, X is N, Y is C—H, and the values for $R^1$ and $R^6$ are as given in the Table B Table 1.54: A compound of formula (I), wherein $R^2$ is difluorchloromethoxy W is C—H, X is N, Y is C—H, and the values for $R^1$ and $R^6$ are as given in the Table B Table 1.55: A compound of formula (I), wherein $R^2$ is dichloromethoxy, W is C—H, X is N, Y is C—H, and the values for $R^1$ and $R^6$ are as given in the Table B Table 1.56: A compound of formula (I), wherein $R^2$ is monochloromethoxy, W is C—H, X is N, Y is C—H, and the values for $R^1$ and $R^6$ are as given in the Table B Table 1.57: A compound of formula (I), wherein $R^2$ is ethoxy, W is C—H, X is N, Y is C—H, and the values for $R^1$ and $R^6$ are as given in the Table B Table 1.58: A compound of formula (I), wherein $R^2$ is $OCH_2$—$OCH_3$, W is C—H, X is N, Y is C—H, and the values for $R^1$ and $R^6$ are as given in the Table B Table 1.59: A compound of formula (I), wherein $R^2$ is difluorochloromethyl, W is C—H, X is N, Y is C—H, and the values for $R^1$ and $R^6$ are as given in the Table B Table 1.60: A compound of formula (I), wherein $R^2$ is difluoromethyl, W is C—H, X is N, Y is C—H, and the values for $R^1$ and $R^6$ are as given in the Table B

TABLE A

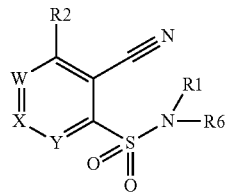

| Nr | R¹ and R⁶ together with the adjacent nitrogen forms |
|---|---|
| A1.1 | 7-Methyl-decahydro-[1,7]naphthyridin-1-yl |
| A1.2 | 1-Methyl-decahydro-[l,7]naphthyridin-7-yl |
| A1.3 | Morpholin-4-yl |
| A1.4 | Thiomorpholin-4-yl |
| A1.5 | 7-Methyl-decahydro-[2,7]naphthyridin-2-yl |
| A1.6 | 2-Methyl-decahydro-[2,7]naphthyridin-7-yl |
| A1.7 | Hexahydro-pyrazino[2,1-c][1,4]oxazin-3-on-8-yl |
| A1.8 | 2-Oxa-5-azabicyclo[2.2.1]heptan-5-yl |
| A1.9 | 2-Thia-5-azabicyclo[2.2.1]heptan-5-yl |
| A1.10 | 5-Methyl-2,5-diazabicyclo[2.2.1]heptan-2-yl |
| A1.11 | 4-Acyl-piperazin-1-yl |
| A1.12 | Morpholin-2-on-4-yl |
| A1.13 | Thiazolidin-3-yl |
| A1.14 | 1,4-Dimethyl-decahydro-pyrido[3,4-b]pyrazine |
| A1.15 | Hexahydro-azepin-1-yl |
| A1.16 | Hexahydro-thiazepin-4-yl |
| A1.17 | Octahydro-benzo[1,4]oxazin-4-yl |
| A1.18 | Hexahydro-1,4-oxazepin-4-yl |
| A1.19 | 4-Methyl-hexahydro-1,4-diazepin-1-yl |
| A1.20 | 1,4-Diazabicyclo[3.2.1]octan-2-on-4-yl |
| A1.21 | 1,3-Diazabicyclo[3.2.2]nonan-3-yl |
| A1.22 | 1,4-Diazabicyclo[3.2.1]octan-4-yl |
| A1.23 | Piperazin-2-on-4-yl |
| A1.24 | Octahydro-furo[3,4-b]pyridin-1-yl |
| A1.25 | Octahydro-furo[3,4-c]pyridin-5-yl |
| A1.26 | 5-Methyl-octahydro-pyrrolo[3,4-c]pyrrol-2-yl |
| A1.27 | Octahydro-pyrrolo[1,2-a]pyrimidin-1-yl |
| A1.28 | 1,3-diethyl-tetrahydro-1,3,5-triazin-2-on-5-yl |
| A1.29 | 5-Methyl-octahydro-1,5-diazocin-1-yl |
| A1.30 | Hexahydro-2H-1,5-thiazocin-5-yl |
| A1.31 | Hexahydro-2H-1,5-oxazocin-5-yl |
| A1.32 | Tetrahydro-2H-1,3-thiazin-3-yl |
| A1.33 | Tetrahydro-2H-1,3-oxazin-3-yl |
| A1.34 | Oxazolidin-5-on-3-yl |
| A1.35 | Isoxazolindin-5-on-2-yl |
| A1.36 | Isoxazolidin-2-yl |
| A1.37 | 2-Methyl-hexahydro-pyridazin-1-yl |
| A1.38 | Tetrahydro-2H-1,2-oxazin-2-yl |
| A1.39 | 2-Methyl-pyrazolidin-1-yl |
| A1.40 | 3-Pyrazolidin-3-on-2-yl |
| A1.41 | 3-Methyl-tetrahydro-1,3,4-oxadiazin-4-yl |
| A1.42 | Tetrahydro-1,2-oxazin-6-on-3-yl |
| A1.43 | Diaziridin-1-yl |
| A1.44 | Piperidin-4-on-1-yl |
| A1.45 | Piperidin-3-on-1-yl |
| A1.46 | Pyrrolidin-3-on-1-yl |
| A1.47 | Hexahydro-3H-azepin-3-on-1-yl |
| A1.48 | Hexahydro-4H-azepin-4-on-1-yl |

TABLE B

| Nr | R¹ and R⁶ together with the adjacent nitrogen forms |
|---|---|
| B1. 1 | Morpholin-4-yl |
| B1. 2 | Thiomorpholin-4-yl |
| B1. 3 | 4-Acyl-piperazin-1-yl |
| B1. 4 | Morpholin-2-on-4-yl |
| B1. 5 | Thiazolidin-3-yl |
| B1. 6 | Hexahydro-azepin-1-yl |
| B1. 7 | Hexahydro-thiazepin-4-yl |
| B1. 8 | Hexahydro-1,4-oxazepin-4-yl |
| B1. 9 | 4-Methyl-hexahydro-1,4-diazepin-1-yl |
| B1. 10 | Piperazin-2-on-4-yl |
| B1. 11 | Tetrahydro-2H-1,3-thiazin-3-yl |
| B1. 12 | Tetrahydro-2H-1,3-oxazin-3-yl |
| B1. 13 | Oxazolidin-5-on-3-yl |
| B1. 14 | Isoxazolindin-5-on-2-yl |
| B1. 15 | Isoxazolidin-2-yl |
| B1. 16 | 2-Methyl-hexahydro-pyridazin-1-yl |
| B1. 17 | Tetrahydro-2H-1,2-oxazin-2-yl |
| B1. 18 | 2-Methyl-pyrazolidin-1-yl |
| B1. 19 | 3-Pyrazolidin-3-on-2-yl |
| B1. 20 | 3-Methyl-tetrahydro-1,3,4-oxadiazin-4-yl |
| B1. 21 | Tetrahydro-1,2-oxazin-6-on-3-yl |
| B1. 22 | Diaziridin-1-yl |
| B1. 23 | Piperidin-4-on-1-yl |
| B1. 24 | Piperidin-3-on-1-yl |
| B1. 25 | Pyrrolidin-3-on-1-yl |
| B1. 26 | Hexahydro-3H-azepin-3-on-1-yl |
| B1. 27 | Hexahydro-4H-azepin-4-on-1-yl |

Compounds of formula I, in which W, X, Y, $R^2$, R1 and $R^6$ are defined as in the first aspect (i.e. any one of W, X and Y can be, for example, CH, N or NO) can be prepared by reacting 2-cyano-sulfonyl halides A with ammonia or a primary or secondary amine B. Hal is halogen, preferably chlorine or bromine, most preferred chlorine (see scheme 1).

Scheme 1

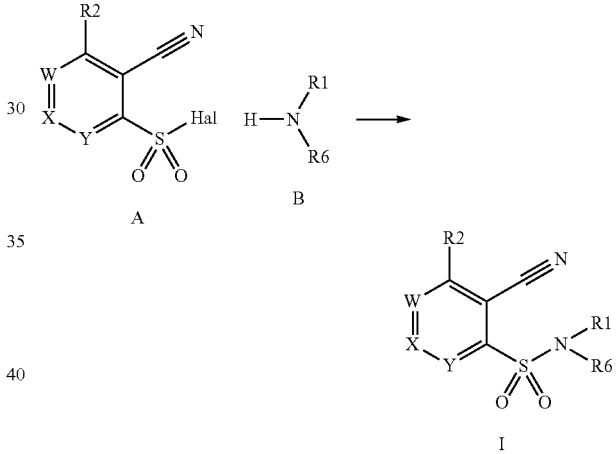

These reactions can be carried out similarly to standard methods described in the past, for example in the publication by Duphar EP 33984 or in the literature by G. Cignarella and U. Teotino, J. Am. Chem. Soc. 1960, 82, 1594-1596.

In general, the 1-2 equivalents of amine B is used based on the sulfonyl halide A. It may be advantageous to perform the reaction in the presence of an auxiliary base. Suitable auxiliary bases include organic bases, for example tertiary amines, such as aliphatic tertiary amines, such as triethylamine or diisopropylethylamine or aromatic bases, such as pyridine.

The reaction is usually carried out in the presence of a solvent. Suitable solvents are alcohols, such as methanol or ethanol, dialkylethers, such as diethylether, diisopropylether or tert-butylmethylether, cyclic ethers, such as dioxane or tetrahydrofuran, N,N-dimethylformamide, acetonitrile, water (provided that the sulfonyl halide A is sufficiently resistant to hydrolysis) or a mixture of these solvents.

The reaction of the amine B and the sulfonylhalide A is usually carried out at a reaction temperature ranging from 0° C. to the boiling point of the solvent, preferably from 0° C. to 30° C.

If not commercially available the amines B can be prepared by methods known to a person skilled in the art.

New 2-cyano-sulfonylhalides can be prepared by the methods described hereafter. Similar to procedures described in *J. Med. Chem.* 1990, 33, 434-444 by N. V. Harris et al. compounds D', E, F and G, preferably when W, X and Y are each C—H, can be prepared starting from compound C. These intermediates D', E, F and G can be transformed into the sulfonyl halide A using standard procedures (scheme 2), for example as described in the publication WO06/056433 by BASF or in the literature in *Helv. Chim. Acta* 1976, 59(42-43), 379-387 by A. Courtin.

to 45° C. In order to complete the reaction, after the evolution of nitrogen has ceased, the reaction temperature can be raised to 80° C. to 90° C.

d¹) In general, 1-2 equivalents of MOD, in which M is an alkali cation, such as a sodium cation, a potassium cation or a caesium cation, O is oxygen and D (a C1-C6-alkyl radical which may be substituted) is reacted with compound F.

MOD, in which M is an alkali cation, such as a sodium cation, a potassium cation or a caesium cation, O is oxygen and D (a C1-C6-alkyl radical which may be halogen substi- Scheme 2

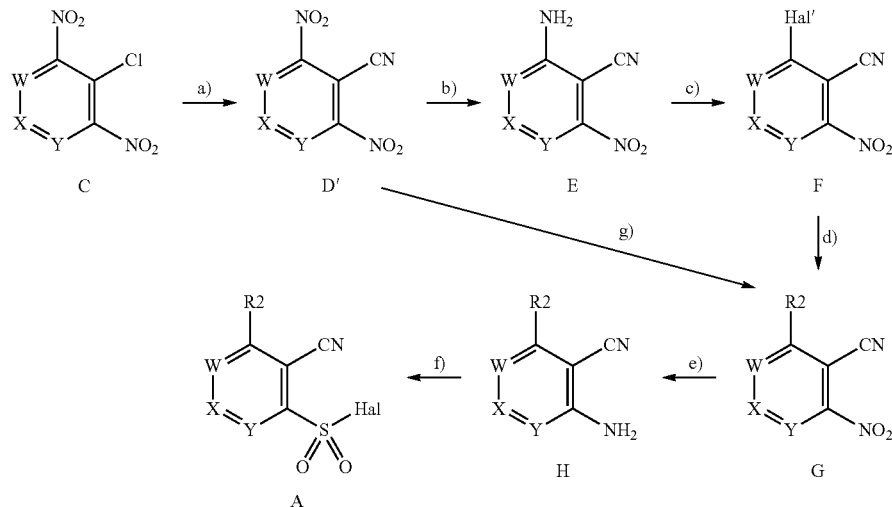

a) The chlorine atom in compound C can be replaced by a cyano group to afford compound D'.

In general, the 1-2 equivalents of copper (I) cyanide or sodium cyanide is used based on the compound C.

The reaction is usually carried out in the presence of a solvent. Suitable solvents are cyclic ethers, such as dioxane or tetrahydrofuran, N,N-dimethylformamide, acetonitrile, water or a mixture of these solvents.

The reaction of the compound C and the copper (I) cyanide is usually carried out at a reaction temperature ranging from 0° C. to the boiling point of the solvent, preferably in N,N-dimethylformamide at 140° C. to 150° C.

b) In general, the reduction of one nitro group in compound D' is achieved with a 1.5-3 fold excess of iron powder in the presence of a concentrated acid, such as hydrochloric acid.

The reaction is usually carried out in the presence of a solvent. Suitable solvents are alcohols, such as methanol or ethanol, cyclic ethers, such as dioxane or tetrahydrofuran, water or a mixture of these solvents.

The reduction is usually carried out at a reaction temperature ranging from 0° C. to the boiling point of the solvent, preferably at 70° C. to 90° C.

c) In general, the amino group in compound E can be transformed into a halogen group, such as bromide or chloride, by treating compound E with 1-1.5 equivalents of sodium nitrite in the presence of a concentrated acid, such as sulfuric acid, glacial acetic acid, hydrochloric acid hydrobromic acid or mixtures thereof, followed by addition of 1-2 equivalents of copper(I) halide, such as copper(I) bromide or copper(I) chloride.

The transformation is usually carried out at a reaction temperature ranging from 0° C. to 50° C., preferably at 30° C.

tuted), can be prepared by reacting HOD with an alkali metal, such as sodium or an alkali hydride, such as sodium hydride.

The reaction is usually carried out in the presence of a solvent. Suitable solvents are HOD, cyclic ethers, such as dioxane or tetrahydrofuran, N,N-dimethylformamide, N,N-dimethylacetamide, acetonitrile, dimethylsulfoxide, water or a mixture of these solvents.

The reaction is usually carried out at a reaction temperature ranging from 0° C. to the boiling point of the solvent, preferably at 80° C. to 100° C.

d²) In general, compound F reacts with 1-2 equivalents of a boronic acid, a tin compound or a zinc compound in the presence of catalytical amounts of a palladium catalyst, such as palladium tetrakistriphenylphosphine.

The reaction is usually carried out in the presence of a solvent. Suitable solvents, depending on the reagent used, are alcohols, such as methanol or ethanol, dialkylethers, such as diethylether, diisopropylether or tert-butylmethylether, cyclic ethers, such as dioxane or tetrahydrofuran, N,N-dimethylformamide, dimethylformamide, 1,2-dimethoxyethane, acetonitrile, toluene, water or a mixture of these solvents.

The reaction is usually carried out in the presence of a base, when boronic acids are used. Suitable bases are sodium carbonate, potassium carbonate, sodium acetate, potassium phosphate or sodium tert.-butanolate.

The reaction is usually carried out at a reaction temperature ranging from 0° C. to the boiling point of the solvent, preferably at 80° C. to 100° C.

e) In general, the reduction of the nitro group in compound G is achieved with a 1.5-3 fold excess of iron powder in the presence of a concentrated acid, such as hydrochloric acid.

The reaction is usually carried out in the presence of a solvent. Suitable solvents are alcohols, such as methanol or ethanol, cyclic ethers, such as dioxane or tetrahydrofuran, water or a mixture of these solvents.

The reduction is usually carried out at a reaction temperature ranging from 0° C. to the boiling point of the solvent, preferably at 70° C. to 90° C.

f) The amino group in compound H is converted into the corresponding diazonium salt followed by reacting the diazonium salt with sulfur dioxide in the presence of cupric(II) chloride to afford the sulfonylchloride A.

Suitable nitrosating agents are nitrosium tetrafluoroborate, nitrosyl chloride, nitrosyl sulfuric acid, alkyl nitrites, such as tert.-butyl nitrite, or salts of nitrous acid, such as sodium nitrite. Preferably sodium nitrite is used.

In general, sulfur dioxide is dissolved in glacial acetic acid.

The diazonium salt can also react with a mixture of cupric (I) cyanate and sodium cyanate to afford the cyanate compound, which is treated with sodium sulfide to afford the disulfide compound. The disulfide compound is converted with nitrous acid in the presence of chlorine into the sulfonylchloride A.

g) If $R^2$ is OD, the nitro compound D' can be transformed into compound G.

In general, 1-2 equivalents of MOD, in which M is an alkali cation, such as a sodium cation, a potassium cation or a caesium cation, O is oxygen and D is as defined above, is reacted with compound P.

MOD, in which M is an alkali cation, such as a sodium cation, a potassium cation or a caesium cation, O is oxygen and D is as defined above, can be prepared by reacting HOD with an alkali metal, such as sodium or an alkali hydride, such as sodium hydride.

The reaction is usually carried out in the presence of a solvent. Suitable solvents are HOD, cyclic ethers, such as dioxane or tetrahydrofuran, N,N-dimethylformamide, N,N-dimethylacetamide, acetonitrile, dimethylsulfoxide, water or a mixture of these solvents.

The reaction is usually carried out at a reaction temperature ranging from 0° C. to the boiling point of the solvent, preferably at 80° C. to 100° C.

Similar to standard procedures, for example as described in the publication WO07/014,913 by BASF, compounds K, L, M and A can be prepared starting from compound J (when W, X, Y and $R^2$ are as defined in the first aspect), preferably when W and Y are CH and X is N (scheme 3).

Scheme 3 h) The aldehyde J can be transformed with 1-2 equivalents of hydroxylammonium chloride into its oxime.

The reaction is usually carried out in the presence of a solvent. Suitable solvents are alcohols, such as methanol, ethanol, iso-propanol, or a mixture of these solvents.

In general the reaction is performed in the presence of a base. Suitable bases include organic bases, for example tertiary amines, such as aliphatic tertiary amines, such as triethylamine or diisopropylethylamine or aromatic bases, such as pyridine.

The reaction is usually carried out at a reaction temperature ranging from 0° C. to the boiling point of the solvent, preferably at 80° C. to 100° C.

Dehydration of the oxime to the cyano compound K can be achieved by treating the oxime with acetic anhydride.

The reaction is usually carried out at a reaction temperature ranging from 0° C. to the boiling point of the solvent, preferably under refluxing conditions.

i) The halogen, preferably chlorine or fluorine in compound K, can be converted into its thioether in compound L, in which R is C1-C4-alkyl or aryl, such as propyl or iso-propyl or benzyl.

In general, compound K is reacted with 1-2 equivalents of alkyl or benzyl mercaptan.

The reaction is usually carried out in the presence of a solvent. Suitable solvents are dialkylethers, such as diethylether, diisopropylether or tert-butylmethylether, cyclic ethers, such as dioxane or tetrahydrofuran, N,N-dimethylformamide, acetonitrile or a mixture of these solvents.

In general, the reaction is performed in the presence of a base. Suitable bases are metal hydrides, such as sodium hydride, or metal carbonates, such as lithium carbonate, sodium carbonate, potassium carbonate or calcium carbonate or metal hydrogen carbonates, such as sodium hydrogen carbonate.

The reaction is usually carried out at a reaction temperature ranging from 0° C. to the boiling point of the solvent.

$j^1$) In general, 1-2 equivalents of MOD, in which M is an alkali cation, such as a sodium cation, a potassium cation or a caesium cation, O is oxygen and D is as defined above is reacted with compound L.

MOD, in which M is an alkali cation, such as a sodium cation, a potassium cation or a caesium cation, O is oxygen and D is as defined above, can be prepared by reacting HOD with an alkali metal, such as sodium or an alkali hydride, such as sodium hydride.

The reaction is usually carried out in the presence of a solvent. Suitable solvents are HOD, cyclic ethers, such as dioxane or tetrahydrofuran, N,N-dimethylformamide, N,N-dimethylacetamide, acetonitrile, dimethylsulfoxide, water or a mixture of these solvents.

The reaction is usually carried out at a reaction temperature ranging from 0° C. to the boiling point of the solvent, preferably at 80° C. to 100° C.

j²) In general, compound L reacts with 1-2 equivalents of a boronic acid, a tin compound or a zinc compound in the presence of catalytical amounts of a palladium catalyst, such as palladium tetrakistriphenylphosphine.

The reaction is usually carried out in the presence of a solvent. Suitable solvents, depending on the reagent used, are alcohols, such as methanol or ethanol, dialkylethers, such as diethylether, diisopropylether or tert-butylmethylether, cyclic ethers, such as dioxane or tetrahydrofuran, N,N-dimethylformamide, dimethylformamide, 1,2-dimethoxyethane, acetonitrile, toluene, water or a mixture of these solvents.

The reaction is usually carried out in the presence of a base, when boronic acids are used. Suitable bases are sodium carbonate, potassium carbonate, sodium acetate, potassium phosphate or sodium tert.-butanolate.

The reaction is usually carried out at a reaction temperature ranging from 0° C. to the boiling point of the solvent, preferably at 80° C. to 100° C.

k) Oxidative cleavage of the thioether compound M in order to receive the sulfonyl halide A, in which Hal is chlorine, is usually performed by reacting compound M with chlorine gas.

The reaction is usually carried out in the presence of a solvent. Suitable solvents are halogenated organic solvents, such as chloroform, phenylchloride, acetic acid, water or a preferably a mixture of 2 or 3 of these solvents.

The dihalo compound J can be prepared similar to procedures described in the literature, for example in *Heterocycles* 1995, 41(4), 675-88 by V. Bertini or known to the person skilled in the art.

The substituent $R^2$ or other substituents $R^3$, $R^4$ or $R^5$ can be introduced at a later stage or at the end of the synthesis in order to obtain new sulfonamides of the structure I. This is recommended, especially if the substituents are not stable under the reaction conditions described above. As an example the introduction of the group $R^2$ is shown in scheme 4.

l) Nitro compound F can be reduced to the amino compound N. In general, the reduction of the nitro group in compound F is achieved with a 1.5-3 fold excess of iron powder in the presence of a concentrated acid, such as hydrochloric acid.

The reaction is usually carried out in the presence of a solvent. Suitable solvents are alcohols, such as methanol or ethanol, cyclic ethers, such as dioxane or tetrahydrofuran, water or a mixture of these solvents.

The reduction is usually carried out at a reaction temperature ranging from 0° C. to the boiling point of the solvent, preferably at 70° C. to 90° C.

m) The amino group in compound N is converted into the corresponding diazonium salt followed by reacting the diazonium salt with dioxide in the presence of cupric(II) chloride to afford the sulfonylchloride P.

Suitable nitrosating agents are nitrosium tetrafluoroborate, nitrosyl chloride, nitrosyl sulfuric acid, alkyl nitrites, such as tert.-butyl nitrite, or salts of nitrous acid, such as sodium nitrite. Preferably sodium nitrite is used.

In general, sulfur dioxide is dissolved in glacial acetic acid.

The diazonium salt can also react with a mixture of cupric (I) cyanate and sodium cyanate to afford the cyanate compound, which is treated with sodium sulfide to afford the disulfide compound. The disulfide compound is converted with nitrous acid in the presence of chlorine into the sulfonylchloride P.

n) The sulfonyl chloride P is reacted to the sulfonamide Q. In general, the 1-2 equivalents of amine is used based on the sulfonyl halide P. It may be advantageous to perform the reaction in the presence of an auxiliary base. Suitable auxiliary bases include organic bases, for example tertiary amines, such as aliphatic tertiary amines, such as triethylamine or diisopropylethylamine or aromatic bases, such as pyridine.

The reaction is usually carried out in the presence of a solvent. Suitable solvents are alcohols, such as methanol or

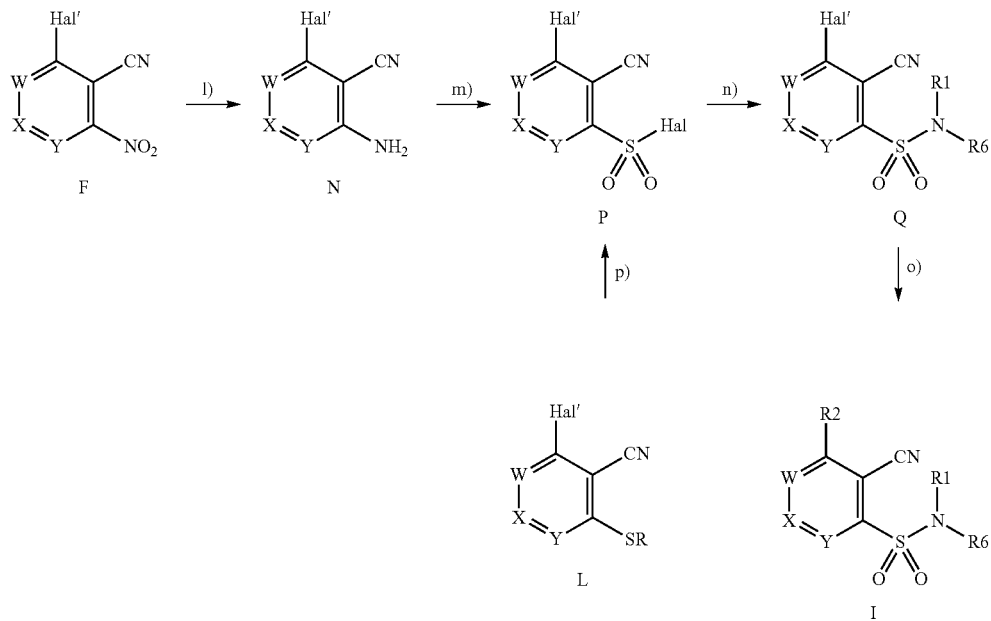

Scheme 4 ethanol, dialkylethers, such as diethylether, diisopropylether or tert-butylmethylether, cyclic ethers, such as dioxane or tetrahydrofuran, N,N-dimethylformamide, acetonitrile, water (provided that the sulfonyl halide A is sufficiently resistant to hydrolysis) or a mixture of these solvents.

The reaction of the amine and the sulfonylhalide P is usually carried out at a reaction temperature ranging from 0° C. to the boiling point of the solvent, preferably from 0° C. to 30° C.

If not commercially available the amines can be prepared by standard methods for preparing primary or secondary amines.

$o^1$) In general, 1-2 equivalents of MOD, in which M is an alkali cation, such as a sodium cation, a potassium cation or a caesium cation, O is oxygen and D is as defined above, is reacted with compound P.

MOD, in which M is an alkali cation, such as a sodium cation, a potassium cation or a caesium cation, O is oxygen and D is as defined above, can be prepared by reacting HOD with an alkali metal, such as sodium or an alkali hydride, such as sodium hydride.

The reaction is usually carried out in the presence of a solvent. Suitable solvents are HOD, cyclic ethers, such as dioxane or tetrahydrofuran, N,N-dimethylformamide, N,N-dimethylacetamide, acetonitrile, dimethylsulfoxide, water or a mixture of these solvents.

The reaction is usually carried out at a reaction temperature ranging from 0° C. to the boiling point of the solvent, preferably at 80° C. to 100° C.

$o^2$) In general, compound P reacts with 1-2 equivalents of a boronic acid, a tin compound or a zinc compound in the presence of catalytical amounts of a palladium catalyst, such as palladium tetrakistriphenylphosphine.

The reaction is usually carried out in the presence of a solvent. Suitable solvents, depending on the reagent used, are alcohols, such as methanol or ethanol, dialkylethers, such as diethylether, diisopropylether or tert-butylmethylether, cyclic ethers, such as dioxane or tetrahydrofuran, N,N-dimethylformamide, dimethylformamide, 1,2-dimethoxyethane, acetonitrile, toluene, water or a mixture of these solvents.

The reaction is usually carried out in the presence of a base, when boronic acids are used. Suitable bases are sodium carbonate, potassium carbonate, sodium acetate, potassium phosphate or sodium tert.-butanolate.

The reaction is usually carried out at a reaction temperature ranging from 0° C. to the boiling point of the solvent, preferably at 80° C. to 100° C.

p) The intermediate P, in which Hal is chlorine, can be also prepared reacting L with chlorine.

The reaction is usually carried out in the presence of a solvent. Suitable solvents are halogenated organic solvents, such as chloroform, phenylchloride, acetic acid, water or a preferably a mixture of 2 or 3 of these solvents.

Another possibilty to introduce $R^2$ in the end of the synthesis, when $R^2$ is OD (D is a C1-C6-alkyl radical which may be halogen substituted), especially when W, X and Y are each $CR^3$, $CR^4$ and $CR^5$ respectively, is shown in scheme 5.

Scheme 5

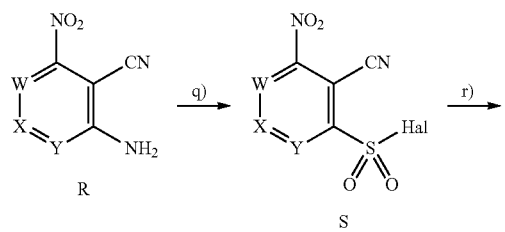

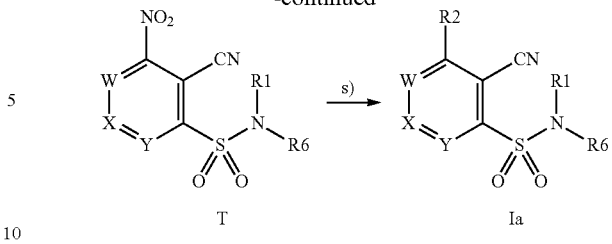

q) The amino group in compound R is converted into the corresponding diazonium salt followed by reacting the diazonium salt with dioxide in the presence of cupric(II)chloride to afford the sulfonylchloride S.

Suitable nitrosating agents are nitrosium tetrafluoroborate, nitrosyl chloride, nitrosyl sulfuric acid, alkyl nitrites, such as tert.-butyl nitrite, or salts of nitrous acid, such as sodium nitrite. Preferably sodium nitrite is used.

In general, sulfur dioxide is dissolved in glacial acetic acid.

The diazonium salt can also react with a mixture of cupric (I) cyanate and sodium cyanate to afford the cyanate compound, which is treated with sodium sulfide to afford the disulfide compound. The disulfide compound is converted with nitrous acid in the presence of chlorine into the sulfonylchloride S.

r) The sulfonyl chloride S is reacted to the sulfonamide T (an embodiment of formula I). In general, the 1-2 equivalents of amine is used based on the sulfonyl halide S. It may be advantageous to perform the reaction in the presence of an auxiliary base. Suitable auxiliary bases include organic bases, for example tertiary amines, such as aliphatic tertiary amines, such as triethylamine or diisopropylethylamine or aromatic bases, such as pyridine.

The reaction is usually carried out in the presence of a solvent. Suitable solvents are alcohols, such as methanol or ethanol, dialkylethers, such as diethylether, diisopropylether or tert-butylmethylether, cyclic ethers, such as dioxane or tetrahydrofuran, N,N-dimethylformamide, acetonitrile, water (provided that the sulfonyl halide A is sufficiently resistant to hydrolysis) or a mixture of these solvents.

The reaction of the amine and the sulfonylhalide S is usually carried out at a reaction temperature ranging from 0° C. to the boiling point of the solvent, preferably from 0° C. to 30° C.

If not commercially available the amines can be prepared by standard methods for preparing primary or secondary amines.

s) In general, 1-2 equivalents of MOD, in which M is an alkali cation, such as a sodium cation, a potassium cation or a caesium cation, O is oxygen and D is as defined above is reacted with compound T.

MOD, in which M is an alkali cation, such as a sodium cation, a potassium cation or a caesium cation, O is oxygen and D is as defined above, can be prepared by reacting HOD with an alkali metal, such as sodium or an alkali hydride, such as sodium hydride.

The reaction is usually carried out in the presence of a solvent. Suitable solvents are HOD, cyclic ethers, such as dioxane or tetrahydrofuran, N,N-dimethylformamide, N,N-dimethylacetamide, acetonitrile, dimethylsulfoxide, water or a mixture of these solvents.

The reaction is usually carried out at a reaction temperature ranging from 0° C. to the boiling point of the solvent, preferably at 80° C. to 100° C.

New 2-cyano-sulfonylhalides can also be prepared by the methods described hereafter (scheme 6).

Scheme 6

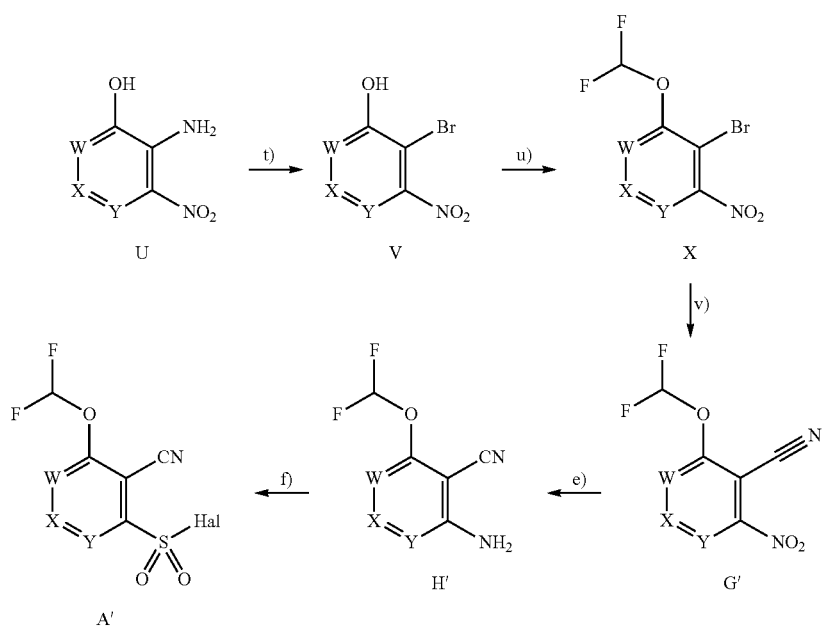

t) In general, the amino group in compound U can be transformed into a halogen group, such as bromide, by treating compound U with 1-1.5 equivalents of sodium nitrite in the presence of a concentrated acid, such as sulfuric acid, glacial acetic acid, hydrochloric acid hydrobromic acid or mixtures thereof, followed by addition of 1-2 equivalents of copper(I) halide, such as copper(I) bromide or copper(I) chloride.

The transformation is usually carried out at a reaction temperature ranging from 0° C. to 50° C., preferably at 30° C. to 45° C. In order to complete the reaction, after the evolution of nitrogen has ceased, the reaction temperature can be raised to 80° C. to 90° C.

u) The difluoromethyl group in compound X can be introduced by alkylating the phenolic group of compound V by treatment with chlorodifluoromethane and a base or by treatment with chlorodifluoro acetic acid or salts thereof and a base.

The reaction is usually carried out in the presence of a solvent. Suitable solvents, depending on the reagent used, are alcohols, such as methanol or ethanol, dialkylethers, such as diethylether, diisopropylether or tert-butylmethylether, cyclic ethers, such as dioxane or tetrahydrofuran, N,N-dimethylformamide, dimethylformamide, 1,2-dimethoxyethane, acetonitrile, toluene, water or a mixture of these solvents.

The reaction is carried out in the presence of a base. Suitable bases are sodium hydroxide, potassium hydroxide, sodium carbonate, potassium carbonate or sodium tert.-butanolate.

The reaction is usually carried out at a reaction temperature ranging from 0° C. to the boiling point of the solvent, preferably at 80° C. to 100° C.

The dihalo compound X can be prepared similar to procedures described in the literature, for example in *Helvetica Chimia Acta* 1995, 88, 1044-1046 or known to the person skilled in the art.

v) The bromine atom in compound X can be replaced by a cyano group to afford compound G'.

In general, the 1-2 equivalents of copper (I) cyanide or sodium cyanide is used based on the compound X'.

The reaction is usually carried out in the presence of a solvent. Suitable solvents are cyclic ethers, such as dioxane or tetrahydrofuran, N,N-dimethylformamide, acetonitrile, water or a mixture of these solvents.

The reaction of the compound X and the copper (I) cyanide is usually carried out at a reaction temperature ranging from 0° C. to the boiling point of the solvent, preferably in N,N-dimethylformamide at 140° C. to 150° C. or at higher temperatures in a sealed tube in a microwave oven.

Thereafter, reaction steps (e) and (f) (described above) afford the corresponding sulfonyl halide.

A skilled person would understand that appropriate changes to reaction conditions described above may be required for a specific cyano-substituted phenyl compounds and the corresponding nitrogenous derivative compounds thereof of formula I.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds I are obtained by treatment with a suitable acid or a suitable ion exchanger reagent and salts with bases are obtained by treatment with a suitable base or with a suitable ion exchanger reagent.

Salts of compounds I can be converted in the customary manner into the free compounds of formula I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

Salts of the compounds of the formula I which are suitable for the use according to the invention are especially agriculturally acceptable salts. They can be formed in a customary method, e.g. by reacting the compound with an acid of the anion in question.

Suitable agriculturally useful salts are especially the salts of those cations or the acid addition salts of those acids whose cations and anions, respectively, do not have any adverse effect on the action of the compounds according to the present invention, which are useful for combating harmful insects, arachnids and/or nematodes. Thus, suitable cations are in particular the ions of the alkali metals, preferably lithium, sodium and potassium, of the alkaline earth metals, preferably calcium, magnesium and barium, and of the transition metals, preferably manganese, copper, zinc and iron, and also the ammonium ion which may, if desired, carry one to four C1-C4-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri(C1-C4-alkyl) sulfonium, and sulfoxonium ions, preferably tri (C1-C4-alkyl) sulfoxonium.

Anions of useful acid addition salts are primarily chloride, bromide, fluoride, hydrogen sulfate, sulfate, dihydrogen phosphate, hydride, hydroxide, hydrogen phosphate, phosphate, nitrate, hydrogen carbonate, carbonate, hexafluorosilicate, hexafluorophosphate, benzoate, and the anions of C1-C4-alkanoic acids, preferably formate, acetate, propionate and butyrate. They can be formed by reacting the compounds of the formula I with an acid of the corresponding anion, preferably of hydrochloric acid, hydrobromic acid, sulfuric acid, phosphoric acid or nitric acid. Also suitable salts include adducts of the formula I, such as maleic acid, dimaleic acid, fumaric acid, difumaric acid, and methane sulfonic acid.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

Also made available herein are novel intermediate compounds to the compounds of formula I.

The compounds I according to the invention are preventively and/or curatively valuable active ingredients in the field of pest control, even at low rates of application, which have a very favorable biocidel spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

The compounds of the formula I (including compounds of formulae Ia, Ib, Ic and Id) and compositions thereof are suitable for efficiently controlling pests from the class Insecta, class Arachnida and/or class Nematoda, particularly in crop protection. In particular, they are suitable for controlling the following animal pests:

Insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;*

Beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Criceris asparagi, Diabrotica balteata, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;*

Dipterans (Diptera), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa;*

Thrips (Thysanoptera), e.g. *Frankliniella fusca, Frankliniella occidentalis, Frankliniella tritici, Scirtothrips citri, Thrips oryzae, Thrips palmi* and *Thrips tabaci;*

Hymenopterans (Hymenoptera), e.g. *Athalia rosae, Atta cephalotes, Atta sexdens, Atta texana, Hoplocampa minuta, Hoplocampa testudinea, Monomorium pharaonis, Solenopsis geminata* and *Solenopsis invicta;*

Heteropterans (Heteroptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor;*

Homopterans (Homoptera), e.g. *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla pin, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand,* and *Viteus vitifolii;*

Termites (Isoptera), e.g. *Calotermes flavicollis, Leucotermes flavipes, Reticulitermes lucifugus* and *Termes natalensis;*

Orthopterans (Orthoptera), e.g. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus;*

Arachnoidea, such as arachnids (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and *Eriophyidae* spp., such as *Aculus schlechtendali, Phyllocoptrata oleivora* and *Eriophyes sheldoni; Tarsonemidae* spp., such as *Phytonemus pallidus* and *Polyphagotarsonemus latus; Tenuipalpidae* spp., such as *Brevipalpus phoenicis; Tetranychidae* spp., such as *Tetranychus cinnabarinus, Tetranychus kanzawai, Tetranychus pacificus, Tetranychus telarius* and *Tetranychus urticae, Panonychus ulmi, Panonychus citri,* and *oligonychus pratensis;* and Nematodes, including plant parasitic nematodes and nematodes living in the soil. Plant parasitic nematodes include, such as root knot nematodes, *Meloidogyne hapla, Meloid-*

*ogyne incognita, Meloidogyne javanica*, and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; *Sting nematodes, Belonolaimus longicaudatus* and other *Belonolaimus* species; *Pine nematodes, Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; *Spiral nematodes, Heliocotylenchus multicinctus* and other *Helicotylenchus* species; Sheath and *sheathoid nematodes, Hemicycliophora* species and *Hemicriconemoides* species; *Hirshmanniella* species; *Lance nematodes, Hoploaimus* species; false rootknot nematodes, *Nacobbus* species; *Needle nematodes, Longidorus elongatus* and other *Longidorus* species; Pin nematodes, *Paratylenchus* species; *Lesion nematodes, Pratylenchus neglectus, Pratylenchus penetrans, Pratylenchus curvitatus, Pratylenchus goodeyi* and other *Pratylenchus* species; *Burrowing nematodes, Radopholus similis* and other *Radopholus* species; *Reniform nematodes, Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; *Citrus nematodes, Tylenchulus* species; *Dagger nematodes, Xiphinema* species; and other plant parasitic nematode species.

The compounds of formula I, and compositions containing them, can also be useful for molluscicidal action, especially against slugs. Molluscs which may be controlled by methods and compositions of the present invention are preferably molluscs comprised in the gastropod class, more preferably the subclass pulmonata, even more preferably snails and slugs, and most preferably include, for example, Ampullariidae; *Arion* (*A. ater, A. circumscriptus, A. hortensis, A. rufus*); Bradybaenidae (*Bradybaena fruticum*); Cepaea (*C. hortensis, C. Nemoralis*); ochlodina; *Deroceras* (*D. agrestis, D. empiricorum, D. laeve, D. reticulatum*); *Discus* (*D. rotundatus*); Euomphalia; *Galba* (*G. trunculata*); *Helicelia* (*H. itala, H. obvia*); Helicidae *Helicigona arbustorum*); *Helicodiscus*; *Helix* (*H. aperta*); *Limax* (*L. cinereoniger, L. flavus, L. marginatus, L. maximus, L. tenellus*); Lymnaea; *Milax* (*M. gagates, M. marginatus, M. sowerbyi*); Opeas; *Pomacea* (*P. canaticulata*); *Vallonia* and *Zanitoides*. The combinations according to the present invention are particularly effective against *Deroceras*, such as *Deroceras reticulatum*.

The compounds of formula I, and compositions containing them, are especially useful for the control of insects and/or nematodes. In particular, the compounds of formula I (especially those disclosed in Table 1.1-1.60), and compositions containing them, can be especially useful for the control of pests selected from the orders Homoptera, Lepidoptera, Diptera, Thysanoptera, and/or Nematoda.

In a preferred embodiment of the invention the compounds of formula I (such as those disclosed in Table 1.1-1.60), and compositions thereof could be used for controlling insects or arachnids, in particular insects of the orders Lepidoptera, Thysanoptera, Coleoptera and/or Homoptera and arachnids of the order Acarina.

The compounds of the formula I (advantageously those disclosed in Tables 1.1-1.60), and compositions thereof according to the present invention could particularly be useful for controlling insects of the order Lepidoptera, Coleoptera, Thysanoptera, Homoptera, and arachnids of the order Acarina, such as *Heliothis* spp., *Thrips* spp., *Diabrotica* spp., *Myzus* spp., *Aphis* spp. *Spodoptera* spp., *Plutella* spp., and *Tetranychidae* spp.

In a further aspect, the present invention relates to a method for controlling a pest in crop protection or for protecting a seed, a plant, parts of a plant and/or plant organs that grow at a later point in time against pest damage which comprises applying a compound of formula I as defined above or a composition thereof to the pest, to the plant, to the seed, to the part of a plant and/or plant organ and/or the environment of each thereof.

For use in a method according to the present invention, the compounds of formula I can be converted into the customary formulations, e.g. solutions, emulsions, suspensions, dusts, powders, pastes, granules and directly sprayable solutions. The use form depends on the particular purpose and application method. Formulations and application methods are chosen to ensure in each case a fine and uniform distribution of the compound of the formula I according to the present invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the compound of formula I with customary formulation auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Solvents/carriers, which are suitable, are e.g.:
solvents such as water, aromatic solvents (for example Solvesso products, xylene and the like), paraffins (for example mineral fractions), alcohols (for example methanol, butanol, pentanol, benzyl alcohol), ketones (for example cyclohexanone, gamma-butyrolactone), pyrrolidones (N-metyhl-pyrrolidone (NMP), N-octylpyrrolidone NOP), acetates (glycol diacetate), alkyl lactates, lactones such as g-butyrolactone, glycols, fatty acid dimethylamides, fatty acids and fatty acid esters, triglycerides, oils of vegetable or animal origin and modified oils such as alkylated plant oils. In principle, solvent mixtures may also be used.

carriers such as ground natural minerals and ground synthetic minerals, such as silica gels, finely divided silicic acid, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters.

Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives are for example dichlorophen and benzyl alcohol hemiformal.

Suitable thickeners are compounds, which confer a pseudoplastic flow behavior to the formulation, i.e. high viscosity at rest and low viscosity in the agitated stage. Mention may be made, in this context, for example, of commercial thickeners based on polysaccharides, such as Xanthan Gum® (Kelzan® from Kelco), Rhodopol®23 (Rhone Poulenc) or Veegum® (from RT. Vanderbilt), or organic phyllosilicates, such as Attaclay® (from Engelhardt).

Antifoam agents suitable for the dispersions according to the invention are, for example, silicone emulsions (such as, for example, Silikon® SRE, Wacker or Rhodorsil® from Rhodia), long-chain alcohols, fatty acids, organofluorine compounds and mixtures thereof. Biocides can be added to stabilize the compositions according to the invention against attack by microorganisms.

Suitable biocides are, for example, based on isothiazolones such as the compounds marketed under the trademarks Proxel® from Avecia (or Arch) or Acticide® RS from Thor Chemie and Kathon® MK from Rohm and Haas.

Suitable antifreeze agents are organic polyols, for example ethylene glycol, propylene glycol or glycerol. These are usually employed in amounts of not more than 10% by weight, based on the total weight of the active compound composition.

If appropriate, the active compound compositions according to the invention may comprise 1 to 5% by weight of buffer, based on the total amount of the formulation prepared, to regulate the pH, the amount and type of the buffer used depending on the chemical properties of the active compound or the active compounds. Examples of buffers are alkali metal salts of weak inorganic or organic acids, such as, for example, phosphoric acid, boronic acid, acetic acid, propionic acid, citric acid, fumaric acid, tartaric acid, oxalic acid and succinic acid.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dusts can be prepared by mixing or concomitantly grinding the active substances with a solid carrier.

Granules, for example coated granules, impregnated granules and homogeneous granules, can be prepared by binding the active ingredients to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

For seed treatment purposes, respective formulations can be diluted 2-10 fold leading to concentrations in the ready to use preparations of 0.01 to 60% by weight active compound by weight, preferably 0.1 to 40% by weight.

The compound of formula I can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from 0.0001 to 10%, preferably from 0.01 to 1% per weight. The active ingredients may also be used successfully in the ultra-low-volume process (ULV), it being possible to apply formulations comprising over 95% by weight of active ingredient, or even to apply the active ingredient without additives.

The following are examples of formulations:
1.
  Products for dilution with water. For seed treatment purposes, such products may be applied to the seed diluted or undiluted.
A) Water-soluble Concentrates (SL, LS)
  10 parts by weight of the active compound is dissolved in 90 parts by weight of water or a water-soluble solvent. As an alternative, wetters or other auxiliaries are added. The active compound dissolves upon dilution with water, whereby a formulation with 10% (w/w) of active compound is obtained.

B) Dispersible Concentrates (DC)

20 parts by weight of the active compound is dissolved in 70 parts by weight of cyclohexanone with addition of 10 parts by weight of a dispersant, for example polyvinylpyrrolidone. Dilution with water gives a dispersion, whereby a formulation with 20% (w/w) of active compounds is obtained.

C) Emulsifiable Concentrates (EC)

15 parts by weight of the active compounds is dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compounds is obtained.

D) Emulsions (EW, EO, ES)

25 parts by weight of the active compound is dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound is obtained.

E) Suspensions (SC, OD, FS)

In an agitated ball mill, 20 parts by weight of the active compound is comminuted with addition of 10 parts by weight of dispersants, wetters and 70 parts by weight of water or of an organic solvent to give a fine active compound suspension. Dilution with water gives a stable suspension of the active compound, whereby a formulation with 20% (w/w) of active compound is obtained.

F) Water-Dispersible Granules and Water-Soluble Granules (WG, SG)

50 parts by weight of the active compound is ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound, whereby a formulation with 50% (w/w) of active compound is obtained.

G) Water-Dispersible Powders and Water-Soluble Powders (WP, SP, SS, WS)

75 parts by weight of the active compound are ground in a rotor-stator mill with addition of 25 parts by weight of dispersants, wetters and silica gel. Dilution with water gives a stable dispersion or solution of the active compound, whereby a formulation with 75% (w/w) of active compound is obtained.

H) Gel-Formulation (GF)

In an agitated ball mill, 20 parts by weight of the active compound is comminuted with addition of 10 parts by weight of dispersants, 1 part by weight of a gelling agent wetters and 70 parts by weight of water or of an organic solvent to give a fine active compound suspension. Dilution with water gives a stable suspension of the active compound, whereby a formulation with 20% (w/w) of active compound is obtained.

2. Products to be applied undiluted for foliar applications. For seed treatment purposes, such products may be applied to the seed diluted or undiluted.

I) Dustable Powders (DP, DS)

5 parts by weight of the active compound are ground finely and mixed intimately with 95 parts by weight of finely divided kaolin. This gives a dustable product having 5% (w/w) of active compound.

J) Granules (GR, FG, GG, MG)

0.5 part by weight of the active compound is ground finely and associated with 95.5 parts by weight of carriers, whereby a formulation with 0.5% (w/w) of active compound is obtained. Current methods are extrusion, spray-drying or the fluidized bed. This gives granules to be applied undiluted for foliar use.

K) ULV solutions (UL)

10 parts by weight of the active compound is dissolved in 90 parts by weight of an organic solvent, for example xylene. This gives a product having 10% (w/w) of active compound, which is applied undiluted for foliar use.

Accordingly, a composition in the form of a formulation comprising a compound of formula I as defined in the first aspect and one or more customary formulation inerts is also provided herein; especially preferred is a seed treatment composition.

Various types of oils, wetters, adjuvants, herbicides, fungicides, other pesticides, or bactericides may be added to the compounds of the invention, if appropriate just immediately prior to use (tank mix). These agents usually are admixed with the agents according to the invention in a weight ratio of 1:10 to 10:1.

In another aspect, the present invention relates to a composition comprising the compound of formula I as defined above and one or more customary formulation auxiliary.

In a further aspect, the present invention relates to a composition comprising the compound of formula I as defined above and one or more active ingredients, and optionally one or more customary formulation auxiliary.

The compounds of formula I and compositions thereof may be applied with other active ingredients, for example with other pesticides, insecticides, fungicides, herbicides, fertilizers such as ammonium nitrate, urea, potash, and superphosphate, phytotoxicants and plant growth regulators, safeners and nematicides. These additional ingredients may be used sequentially or in combination with the above-described active ingredients, if appropriate added only immediately prior to use (tank mix) or provided as a formulated product (pre-mix). For example, the plant(s) may be sprayed with a composition comprising a compound of formula I either before or after being treated with other active ingredients. Generally a combination of active ingredients, including a compound of formula I, are used in seed treatment applications either as tank-mix or pre-mix compositions.

Each additional active ingredient can be admixed with a compound of formula I in a weight ratio of 1:10 to 10:1. In the case of two or more additional active ingredient and a compound of formula I, any two active ingredients (including a compound of formula I) can be in a weight ratio of 1:10 to 10:1. The resulting compositions frequently result in a broader pesticidal spectrum of action.

The following lists (M & F) of pesticides together with which the compounds of formula I according to the invention can be used and with which potential synergistic effects might be produced, is intended to illustrate the possible combinations, but not to impose any limitation:

M.1. Organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

M.2. Carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

M.3. Pyrethroids: allethrin, bifenthrin, cyfluthrin, cyhalothrin, cyphenothrin, cypermethrin, alpha-cypermethrin, beta-cypermethrin, zeta-cypermethrin, deltamethrin, empenthrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, trans-fluthrin, profluthrin, dimefluthrin;

M.4. Growth regulators: a) chitin synthesis inhibitors: benzoylureas: chlorfluazuron, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

M.5. Nicotinic receptor agonists/antagonists compounds: clothianidin, dinotefuran, imidacloprid, thiamethoxam, nitenpyram, acetamiprid, thiacloprid and AKD-1022;

M.6. GABA antagonist compounds: acetoprole, endosulfan, ethiprole, fipronil, vaniliprole, pyrafluprole, pyriprole, the phenylpyrazole compound of formula $I^2$

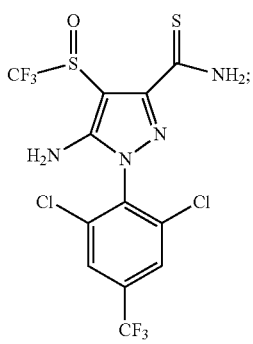

(I$^2$)

M.7. Macrocyclic lactone insecticides: abamectin, emamectin, milbemectin, lepimectin, spinosad;

M.8. METI I compounds: fenazaquin, pyridaben, tebufenpyrad, tolfenpyrad, flufenerim;

M.9. METI II and III compounds: acequinocyl, fluacyprim, hydramethylnon;

M.10. Uncoupler compounds: chlorfenapyr;

M.11. Oxidative phosphorylation inhibitor compounds: cyhexatin, diafenthiuron, fenbutatin oxide, propargite;

M.12. Moulting disruptor compounds: cyromazine;

M.13. Mixed Function Oxidase inhibitor compounds: piperonyl butoxide;

M.14. Sodium channel blocker compounds: indoxacarb, metaflumizone;

M.15. Various: amitraz, benclothiaz, bifenazate, cartap, flonicamid, pyridalyl, pymetrozine, sulfur, thiocyclam, flubendiamide, cyenopyrafen, flupyrazofos, cyflumetofen, amidoflumet, pyrifluquinazon, the aminoquinazolinone compound of formula $I^3$

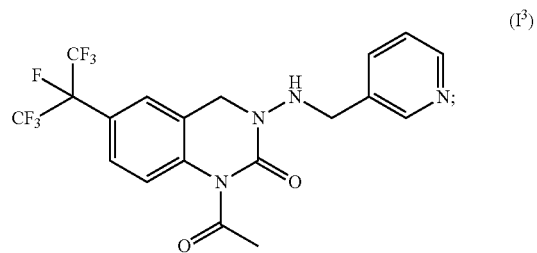 [SMILES: CC(=O)N1C(=O)N(NCc2cccnc2)Cc2cc(C(F)(C(F)(F)F)C(F)(F)F)ccc21]

(I$^3$)

N—R'-2,2-dihalo-1-R''cyclo-propanecarboxamide-2-(2,6-dichloro-alpha,alpha,alpha-tri-fluoro-p-tolyl)hydrazone or N—R'-2,2-di(R''')propionamide-2-(2,6-dichloro-alpha,alpha,alpha-trifluoro-p-tolyl)-hydrazone, wherein R' is methyl or ethyl, halo is chloro or bromo, R'' is hydrogen or methyl and R''' is methyl or ethyl; anthranilamide compounds as chlorantraniliprole or the compound of formula $I^4$

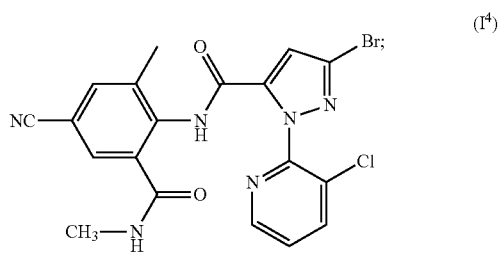 [SMILES: CNC(=O)c1cc(C#N)cc(C)c1NC(=O)c1cc(Br)nn1-c1ncccc1Cl]

(I$^4$)

malononitrile compounds as described in JP 2002 284608, WO 02/89579, WO 02/90320, WO 02/90321, WO 04/06677, WO 04/20399, JP 2004 99597, WO 05/68423, WO 05/68432, or WO 05/63694, especially the malononitrile compounds $CF_3(CH_2)_2C(CN)_2CH_2(CF_2)_3CF_2H$, $CF_3(CH_2)_2C(CN)_2CH_2(CF_2)_5CF_2H$, $CF_3(CH_2)_2C(CN)_2(CH_2)_2C(CF_3)2F$, $CF_3(CH_2)_2C(CN)_2(CH_2)_2(CF_2)_3CF_3$, $CF_2H(CF_2)_3CH_2C(CN)_2CH_2(CF_2)_3CF_2H$, $CF_3(CH_2)_2C(CN)_2CH_2(CF_2)_3CF_3$, $CF_3(CF_2)_2CH_2C(CN)_2CH_2(CF_2)_3CF_2H$, and $CF_3CF_2CH_2C(CN)_2CH_2(CF_2)_3CF_2H$; and compound of formula $I^5$

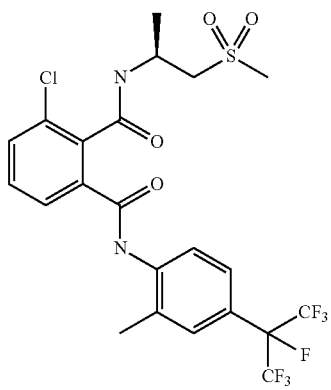

(I$^5$)

as described in WO07/101,601.

The commercially available compounds of the group M may be found in The Pesticide Manual, 13$^{th}$ Edition, British Crop Protection Council (2003) among other publications.

Thioamides of formula $I^2$ and their preparation have been described in WO 98/28279. Lepimectin is known from Agro Project, PJB Publications Ltd, November 2004. Benclothiaz and its preparation have been described in EP-A1 454621. Methidathion and Paraoxon and their preparation have been described in Farm Chemicals Handbook, Volume 88, Meister Publishing Company, 2001. Acetoprole and its preparation have been described in WO 98/28277.

Metaflumizone and its preparation have been described in EP-A1 462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. Cyflumetofen and its preparation have been described in WO 04/080180. The aminoquinazolinone compound of formula $I^3$ has been described in EP A 109 7932. Anthranilamides as the one of formula $I^4$ or as chloranthraniliprole and their preparations have been described in WO 01/70671; WO 02/48137; WO 03/24222, WO 03/15518, WO 04/67528; and WO 04/33468; and WO 05/1 18552. The malononitrile compounds $CF_3(CH_2)_2C(CN)_2CH_2(CF_2)_3CF_2H$, $F3(CH_2)_2C(CN)_2CH_2(CF_2)_5CF_2H$, $CF_3(CH_2)_2C(CN)_2(CH_2)_2C(CF_3)2F$, $F_3(CH_2)_2C(CN)_2(CH_2)_2(CF_2)_3CF_3$, $CF_2H(CF_2)_3CH_2C(CN)_2CH_2(CF_2)_3CF_2H$, $F_3(CH_2)_2C(CN)_2CH_2(CF_2)_3CF_3$, $CF_3(CF_2)_2CH_2C(CN)_2CH_2(CF_2)_3CF_2H$, and $F_3CF_2CH_2C(CN)_2CH_2(CF_2)_3CF_2H$ have been described in WO 05/63694.

Fungicidal mixing partners are those selected from the group F consisting of

F.1 acylalanines such as benalaxyl, metalaxyl, ofurace, oxadixyl;

F.2 amine derivatives such as aldimorph, dodine, dodemorph, fenpropimorph, fenpropidin, guazatine, iminoctadine, spiroxamin, tridemorph;

F.3 anilinopyrimidines such as pyrimethanil, mepanipyrim or cyrodinyl; F.4 antibiotics such as cycloheximid, griseofulvin, kasugamycin, natamycin, polyoxin or streptomycin;

F.5 azoles such as bitertanol, bromoconazole, cyproconazole, difenoconazole, dinitroconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol;

F.6 dicarboximides such as iprodion, myclozolin, procymidon, vinclozolin;

F.7 dithiocarbamates such as ferbam, nabam, maneb, mancozeb, metam, metiram, propineb, polycarbamate, thiram, ziram, zineb;

F.8 heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine;

F.9 copper fungicides such as Bordeaux mixture, copper acetate, copper oxychloride, basic copper sulfate;

F.10 nitrophenyl derivatives such as binapacryl, dinocap, dinobuton, nitrophthalisopropyl;

F.11 phenylpyrroles such as fenpiclonil or fludioxonil;

F.12 strobilurins such as azoxystrobin, dimoxystrobin, fluoxastrobin, kresoxim-methyl, metominostrobin, orysastrobin, picoxystrobin or trifloxystrobin;

F.13 sulfenic acid derivatives such as captafol, captan, dichlofluanid, folpet, tolylfluanid;

F.14 cinnemamides and analogs such as dimethomorph, flumetover or flumorph;

F.15 sulfur, and other fungicides such as acibenzolar-5-methyl, benthiavalicarb, carpropamid, chlorothalonil, cyflufenamid, cymoxanil, dazomet, diclomezin, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid.

Accordingly, a composition comprising a compound of formula I as defined in the first aspect and one or more active ingredients, such as other pesticides (as described above in list M and/or F), insecticides, fungicides, herbicides, fertilizers such as ammonium nitrate, urea, potash, and superphosphate, phytotoxicants and plant growth regulators, safeners and nematicides, and optionally one or more customary formulation inerts is also provided herein; especially preferred is a seed treatment composition.

The animal pest, i.e. the insects, arachnids and nematodes, the plant, seed, soil or water in which the plant is growing can be contacted with the present compound(s) of formula I or composition(s) thereof by any application method known in the art.

The compounds of formula I or the pesticidal compositions thereof may be used to protect growing plants and crops from attack or infestation by animal pests, especially insects, acaridae or arachnids by contacting the plant/crop with a pesticidally effective amount of compounds of formula I. The active ingredients according to the invention can be used for controlling, i.e. containing or destroying, pests of the above-mentioned type which occur in particular on plants, especially on useful plants and ornamentals in agriculture, in horticulture and in forests, or on organs, such as fruits, flowers, foliage, stalks, tubers, seeds, or roots, of such plants, and in some cases even plant organs which are formed at a later point in time remain protected against these pests. The term "crop" refers both to growing and harvested crops.

Suitable target crops are, in particular, cereals, such as wheat, barley, rye, oats, rice, maize (fodder maize and sugar maize/sweet and field corn) or sorghum; beet, such as sugar or fodder beet; fruit, for example pomaceous fruit, stone fruit or soft fruit, such as apples, pears, plums, peaches, bananas, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, iceberg, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants, lawn, turf, fodder grass, and ornamentals, such as petunias, geranium/pelargoniums, pansies and impatiens.

In addition, the compound of formula I may also be used for the treatment of seeds from plants, which tolerate the action of herbicides or fungicides or insecticides owing to breeding, including genetic engineering methods.

For example, crops that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady® and LibertyLink®.

Furthermore, the compound of formula I can be used also for the treatment of plants and seeds, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

Moreover, animal pests may be controlled by contacting the target pest, its food supply, habitat, breeding ground or its locus with a pesticidally effective amount of compounds of formula I. As such, the application may be carried out before or after the infection of the locus, growing crops, or harvested crops by the pest.

The compounds of the invention can also be applied preventively to places at which occurrence of the pests is expected. The compounds of formula I may be also used to protect growing plants from attack or infestation by pests by contacting the plant with a pesticidally effective amount of compounds of formula I. As such, "contacting" includes both direct contact (applying the compounds/compositions directly on the pest and/or plant—typically to the seed, foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds of formula I are effective through both contact (e.g., via soil, glass, wall, bed net, carpet, plant parts or animal parts), and ingestion (bait, or plant part).

For use against ants, termites, wasps, flies, mosquitos, crickets, or cockroaches, compounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

Formulations of compounds of formula I as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250 Degrees C., dimethylformamide, N-methylpyrrolidone, dimethyl sulphoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used. The compounds of formula I and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and its respective compositions also comprise treating surfaces of huts and houses, air spraying and impregnation of curtains, tents, clothing items, bed nets, tsetse-fly trap or the like, Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), $N_1$N-diethylphenylacetamide (DEPA), 1-(3-cyclohexan-1-yl-carbonyl)-2-methylpiperine, (2-hydroxymethyl-cyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bed nets is done in general by dipping the textile material into emulsions or dispersions of the insecticide or spraying them onto the nets.

The compounds of formula I and its compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula I are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

Further areas of use of the compounds of formula I and compositions thereof according to the invention are the protection of stored goods and storerooms and the protection of raw materials, such as wood, textiles, floor coverings or buildings, and also in the hygiene sector, especially the protection of humans, domestic animals and productive livestock against pests of the mentioned type.

In the hygiene sector, compounds of formula I and compositions thereof are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

Compounds of formula I and compositions thereof are also suitable for protecting against insect infestation in the case of materials such as wood, textiles, plastics, adhesives, glues, paints, paper and card, leather, floor coverings and buildings.

In another aspect, the present invention also relates to a method for controlling a pest which comprises applying a compound of formula I as defined above to the pest, material for protection and/or environment thereof. In a first embodiment, the material is selected from a raw material, such as wood, textile, floor covering and building material. In a second embodiment, the pest is controlled against damaging stored goods. In a third embodiment, the pest is controlled in the hygiene sector, especially the protection of humans, domestic animals and productive livestock.

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of compound of formula I per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in bait compositions, the typical content of active ingredient is from 0.001 weight % to 15 weight %, desirably from 0.001 weight % to 5% weight % of compound of formula I.

For use in spray compositions, the content of active ingredient is from 0.001 to 80 weights %, preferably from 0.01 to 50 weight % and most preferably from 0.01 to 15 weight %.

For use in treating crop plants, the rate of application of the active ingredients of this invention may be in the range of 0.1 g to 4000 g per hectare, desirably from 25 g to 600 g per hectare, more desirably from 50 g to 500 g per hectare.

The compounds of formula I are particularly useful for the protection of a seed, for example, from soil pests, and the resulting plant's roots, shoots and foliage against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of a seed, for example, from insects, in particular from soil insects, and of the seedlings' roots, shoots and foliage from insects, in particular from soil and foliar insects, said method comprising contacting, for example, the seeds before sowing and/or after pregermination with a compound of the general formula I or a salt thereof. Particularly preferred is a method, wherein the plant's roots, shoots and/or foliage are protected, more preferably a method, wherein the plants shoots are protected form piercing and sucking insects, most preferably a method, wherein the plants shoots are protected from aphids.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated with or containing a compound of formula I.

The term "coated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient.

Seed treatment comprises all suitable seed treatment techniques known in the art, such as seed dressing, seed coating, seed dusting, seed soaking and seed pelleting. The seed treatment application of the compound formula I can be carried out by any known methods, such as spraying or by dusting the seeds before sowing or during the sowing/planting of the seeds.

Compositions which are especially useful for seed treatment are e.g.:
A Soluble concentrates (SL, LS) D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF) I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter. It may also be applied during the sowing of the seeds.

In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds of formula I for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed treatment formulations may additionally also comprise binders and optionally colorants.

Binders can be added to improve the adhesion of the active materials on the seeds after treatment. Suitable binders are block copolymers EO/PO surfactants but also polyvinylalcoholsl, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers.

Optionally, also colorants can be included in the formulation. Suitable colorants or dyes for seed treatment formulations are Rhodamin B, C.I. Pigment Red 1 12, C.I. Solvent Red 1, pigment blue 15:4, pigment blue 15:3, pigment blue 15:2, pigment blue 15:1, pigment blue 80, pigment yellow 1, pigment yellow 13, pigment red 1 12, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®)

In the treatment of seed, the application rates of the compounds of formula I are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed.

In another aspect, the invention therefore also relates to seed comprising (or treated with) a compound of the formula I as defined above, or an agriculturally useful salt of I, as defined herein. The amount of the compounds of the formula I or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

A material treated with a compound of formula I, therefore, refers to any material, such as for example, a seed, wood, net, In each aspect and embodiment of the invention, "consisting essentially" and inflections thereof are a preferred embodiment of "comprising" and its inflections, and "consisting of" and inflections thereof are a preferred embodiment of "consisting essentially of" and its inflections.

The following Examples are given by way of illustration and not by way of limitation of the invention.

EXAMPLES

Example I1

Preparation of 2-Bromo-3-nitro-phenol

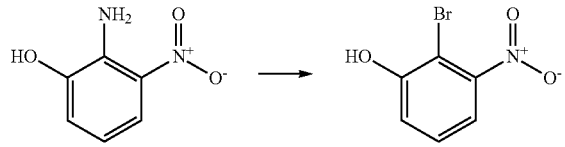 [SMILES: Nc1c(O)cccc1[N+](=O)[O-] ; O=[N+]([O-])c1cccc(O)c1Br]

2-Amino-3-nitrophenol (24.6 g, 160 mmol) is suspended in mixture of water (150 ml) and dioxane (75 ml). At 80° C. hydrobromic acid (48%, 85 ml) is added dropwise. This mixture is stirred at reflux temperature for 30 minutes and then cooled to 0° C. A solution of sodium nitrite (11.04 g, 160 mmol) in water (100 ml) is added dropwise and the reaction mixture is stirred at 0° C. for 1 hour. The reaction mixture is added dropwise to a solution of CuBr (26.4 g, 184 mmol) in water (150 ml) and hydrobromic acid (48%, 85 ml). The resulting suspension is stirred at 0° C. for 30 minutes and at 60° C. for 1 hour. The reaction mixture is cooled to room temperature, diluted with water and extracted three times with ethyl acetate. The combined organic phases are dried over sodium sulfate and concentrated. The residue is purified by column chromatography on silica gel (eluent: dichloromethane/cyclohexane 7:3) to give 2-Bromo-3-nitro-phenol (19.5 g, 56% yield) as a yellow solid. ¹H-NMR (CDCl₃, 400 MHz): 7.50 (d, 1H), 7.35 (t, 1H), 7.25 (d, 1H), 6.05 (s, 1H) ppm.

Example I2

Preparation of 2-Bromo-1-difluoromethoxy-3-nitro-benzene

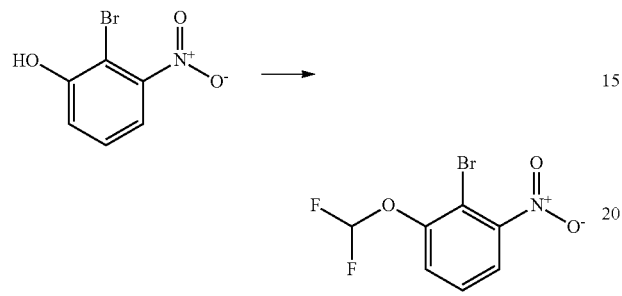

To a mixture of sodium chlorodifluoro acetate (1.29 g, 8.5 mmol) and K₂CO₃ in DMF (5 ml) and water (1.3 ml) is added 2-Bromo-3-nitro-phenol (0.5 g, 2.3 mmol) dissolved in DMF (5 ml) then heated to 100° C. under an argon atmosphere and stirred for 2 hours. The reaction mixture is cooled to room temperature, diluted with water and extracted three times with ethyl acetate. The combined organic phases are dried over sodium sulfate and concentrated to yield 2-Bromo-1-difluoromethoxy-3-nitro-benzene (0.56 g, 91% yield) in pure form. ¹H-NMR (CDCl₃, 400 MHz): 7.65 (m, 1H), 7.45 (m, 2H), 6.60 (t, 1H) ppm.

Example I3

Preparation of 2-Difluoromethoxy-6-nitro-benzonitrile

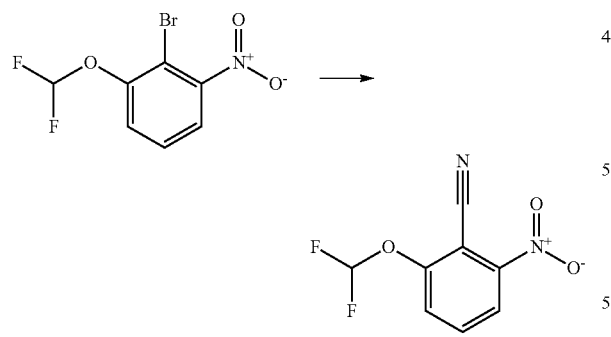

A mixture of 2-bromo-1-difluoromethoxy-3-nitro-benzene (1 g, 3.7 mmol), CuCN (0.40 g, 4.5 mmol) and LiBr (0.32 g, 3.7 mmol) in tetrahydrofuran (10 ml) are heated in a microwave oven at 200° C. for 40 minutes. The reaction mixture is cooled to ambient temperature, diluted with toluene and washed with aqueous sodium bromide (1M) and aqueous sodium hydrogen sulfite (saturated). The organic phase is dried over sodium sulfate and concentrated. The residue is purified by HPLC to give 2-difluoromethoxy-6-nitrobenzonitrile (0.67 g, 84% yield). ¹H-NMR (CDCl₃, 400 MHz): 8.20 (d, 1H), 7.85 (t, 1H), 7.75 (d, 1H), 6.75 (t, 1H) ppm.

Example I4

Preparation of 2-Amino-6-difluoromethoxy-benzonitrile

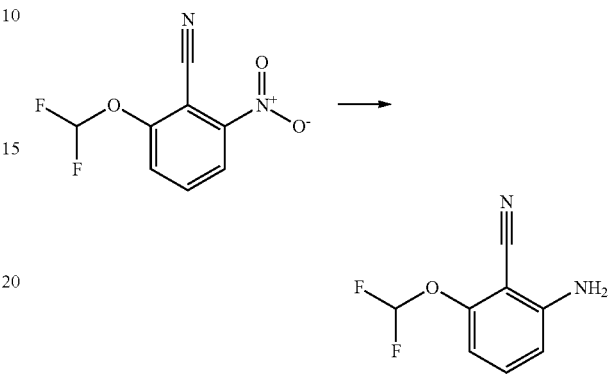

To a solution of 2-difluoromethoxy-6-nitro-benzonitrile (4.0 g, 14.9 mmol) (Example I3) in isopropanol (100 ml) is added tin(II) chloride (10.2 g, 53.6 mmol). Aqueous hydrochloric acid (concentrated) (14.4 ml) is added slowly and the reaction mixture is heated to reflux for 30 minutes. The reaction mixture is cooled to room temperature, diluted with water and the pH is adjusted to 10 by addition of NaOH (2M). The mixture is extracted three times with ethyl acetate. The combined organic phases are dried over sodium sulfate and concentrated to yield 2-amino-6-difluoromethoxy-benzonitrile (3.32 g, 93% yield) in pure form. ¹H-NMR (CDCl₃, 400 MHz): 7.05 (t, 1H), 6.65 (d, 1H), 6.55 (t, 1H), 6.50 (t, 1H), 4.25 (s, br, 2H) ppm.

Example I5

Preparation of 2-Cyano-3-difluoromethoxy-benzenesulfonyl chloride

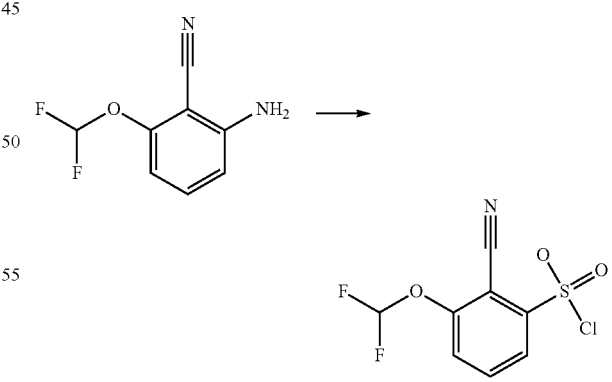

2-Amino-6-difluoromethoxy-benzonitrile (6.4 g, 35 mmol) is dissolved in glacial acetic acid (50 ml). Hydrochloric acid (37%, 12.7 g) is added dropwise at ambient temperature. This mixture is cooled to 5° C. and a solution of sodium nitrite (2.5 g, 36.4 mmol) in Water (8 ml) is added dropwise. The reaction mixture is stirred at 0° C. for 1 hour. The resulting diazonium salt solution is added dropwise at ambient temperature to a mixture of glacial acetic acid (100 ml) saturated at ambient temperature with sulfur dioxide and a solution of CuCl$_2$ (2.18 g, 16.2 mmol) in water (5 ml). The resulting mixture is stirred at ambient temperature for 2 hours. The reaction mixture is poured into an ice/water and extracted three times with dichloromethane. The combined organic phases are dried over sodium sulfate and concentrated to give 2-Cyano-3-difluoromethoxy-benzenesulfonyl chloride (8.5 g, 91% yield) which is used without further purification. $^1$H-NMR (CDCl$_3$, 400 MHz): 8.10 (d, 1H), 7.85 (t, 1H), 7.75 (d, 1H), 6.75 (t, 1H) ppm.

Example I6

General Method for the Synthesis of Sulfonamides

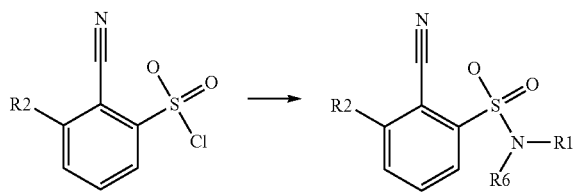

Solution A is prepared by dissolving the amino derivative (0.5 mmol) in acetonitrile (2 ml). Solution B is prepared by dissolving the benzenesulfonyl chloride (1 mmol) in acetonitrile (8 ml). Solution A (0.2 ml, 50 µmol) is put in a well and solution B (0.2 ml, 25 µmol) is added. The mixture is stirred at ambient temperature for 16 hours. The mixture is diluted with acetonitrile (0.2 ml) and then purified by HPLC to give the desired compound.

This general method is used to prepare the compounds of Table P below.

Example I7

Synthesis of 2-Difluoromethoxy-6-(thiazolidine-3-sulfonyl)-benzonitrile

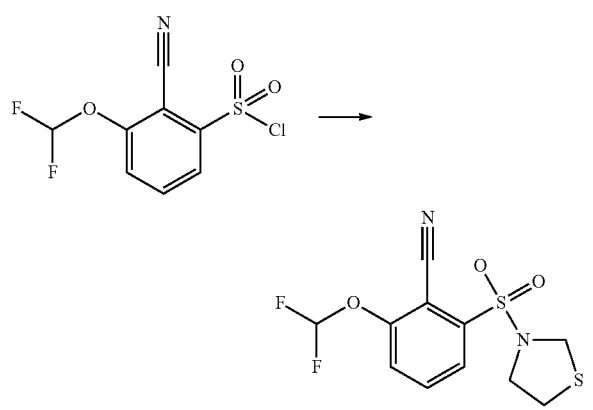

54 mg of 2-cyano-3-difluoromethoxy-benzenesulfonyl chloride in 10 ml of tetrahydrofuran are treated with 32 I of thiazolidine and the mixture is stirred for 16 hours at room temperature. The reaction mixture is concentrated in vacuo. Purification by HPLC affords 35 mg of 2-difluoromethoxy-6-(thiazolidine-3-sulfonyl)-benzonitrile.

Example I8

Synthesis of 2-Fluoro-6-(thiazolidine-3-sulfonyl)-benzonitrile

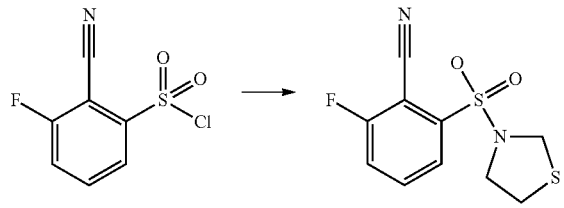

440 mg of 2-cyano-3-fluoro-benzenesulfonyl chloride in 10 ml of tetrahydrofuran are treated with 0.36 ml of thiazolidine and the mixture is stirred for 16 hours at room temperature. The reaction mixture is concentrated in vacuo. Purification by Flash chromatography (eluent: cyclohexane/ethyl acetate 1:1) followed by acidic washing with a 1M HCl solution affords 318 mg of 2-fluoro-6-(thiazolidine-3-sulfonyl)-benzonitrile.

Example I9

Synthesis of 2-Fluoro-6-(1-oxo-1lambda*4*-thiazolidine-3-sulfonyl)-benzonitrile

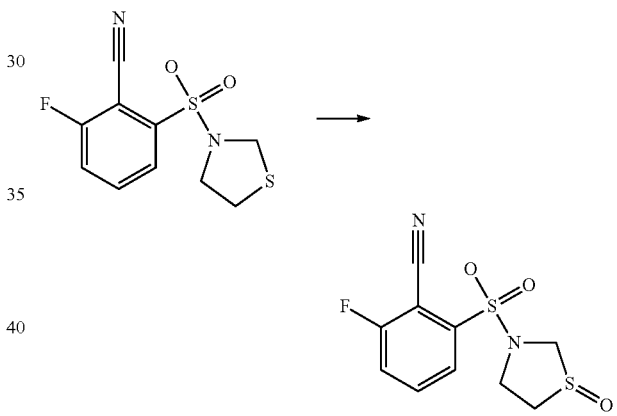

54 mg of 2-Fluoro-6-(thiazolidine-3-sulfonyl)-benzonitrile in 10 ml of methanol and 1 ml of water are treated with 45 mg of sodium periodate, and the mixture is stirred for 14 hours at room temperature. The reaction mixture is poured into water, and the aqueous layer is extracted three times with ethyl acetate. The combined organic layers are dried over sodium sulfate, filtered and concentrated in vacuo. Purification by reverse phase HPLC affords 40 mg of 2-Fluoro-6-(1-oxo-1 lambda*4*-thiazolidine-3-sulfonyl)-benzonitrile.

Example I10

Synthesis of 2-(1,1-Dioxo-1lambda*6*-thiazolidine-3-sulfonyl)-6-fluoro-benzonitrile

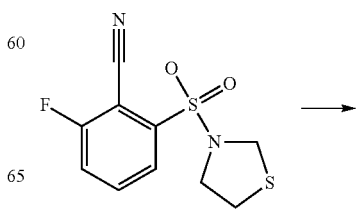

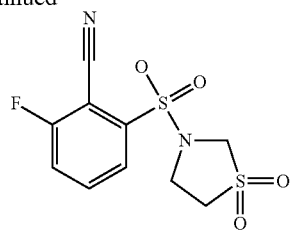

54 mg of 2-Fluoro-6-(thiazolidine-3-sulfonyl)-benzonitrile in 4 ml of dichloromethane are treated with 104 mg of mCPBA (70%), and the mixture is stirred for 14 hours at room temperature. The reaction mixture is washed with a sodium hydrogenocarbonate saturated solution, and the aqueous layer is extracted three times with dichloromethane. The combined organic layers are dried over sodium sulfate, filtered and concentrated in vacuo. Purification by HPLC affords 2-(1,1-Dioxo-1lambda*6*-thiazolidine-3-sulfonyl)-6-fluoro-benzonitrile.

Example I11

Synthesis of 2-Fluoro-6-(3-oxo-pyrrolidine-1-sulfonyl)-benzonitrile

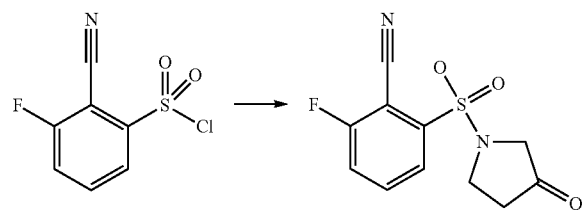

110 mg of 2-cyano-3-fluoro-benzenesulfonyl chloride in 5 ml of tetrahydrofuran are treated with 61 mg of 3-oxo-pyrrolidine hydrochloride and with 0.14 ml of triethylamine, and the mixture is stirred for 16 hours at room temperature. The reaction mixture is concentrated in vacuo, the residue is solved in ethyl acetate and washed with a 1M HCl solution. Purification by Flash chromatography (eluent: cyclohexane/ethyl acetate 1:1) affords 21 mg of 2-fluoro-6-(3-oxo-pyrrolidine-1-sulfonyl)-benzonitrile.

The following methods are used for LC-MS analysis:

Method A: Method (Waters Alliance 2795 LC) with the following HPLC gradient conditions (Solvent A: 0.1% of formic acid in water/acetonitrile (9:1) and Solvent B: 0.1% of formic acid in acetonitrile)

| Time (minutes) | A (%) | B (%) | Flow rate (ml/min) |
|---|---|---|---|
| 0 | 90 | 10 | 1.7 |
| 2.5 | 0 | 100 | 1.7 |
| 2.8 | 0 | 100 | 1.7 |
| 2.9 | 90 | 10 | 1.7 |

Type of column: Waters Atlantis dc18; Column length: 20 mm; Internal diameter of column: 3 mm; Particle Size: 3 micron; Temperature: 40° C.

Method B: Method (Agilent 1100 Series) with the following HPLC gradient conditions (Solvent A: 0.1% of formic acid in water and Solvent B: 0.1% of formic acid in acetonitrile)

| Time (minutes) | A (%) | B (%) | Flow rate (ml/min) |
|---|---|---|---|
| 0 | 80 | 20 | 1.7 |
| 2.5 | 0 | 100 | 1.7 |
| 2.8 | 0 | 100 | 1.7 |
| 2.9 | 90 | 10 | 1.7 |

Type of column: Waters Atlantis dc18; Column length: 20 mm; Internal diameter of column: 3 mm; Particle Size: 3 micron; Temperature: 40° C.

Rf values are measured using cyclohexane/ethyl acetate 1:1 as eluent.

TABLE P

List of the compounds of formula below with characterisations

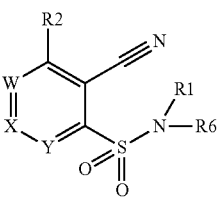

| W | X | Y | R2 | NR1R6 | RT (Min) | M + H | LC/MS Method | Rf |
|---|---|---|---|---|---|---|---|---|
| P1.1 | CH | CH | CH | OCHF$_2$ | 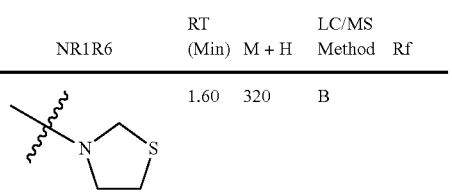 | 1.60 | 320 | B | |
| P1.2 | CH | CH | CH | F | 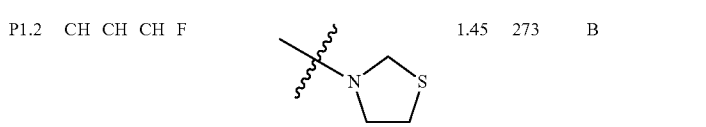 | 1.45 | 273 | B | |

TABLE P-continued

List of the compounds of formula below with characterisations

| | W | X | Y | R2 | NR1R6 | RT (Min) | M+H | LC/MS Method | Rf |
|---|---|---|---|---|---|---|---|---|---|
| P1.3 | CH | CH | CH | OMe | | 1.51 | 285 | B | |
| P1.4 | CH | CH | CH | Me | | 1.57 | 269 | B | |
| P1.5 | CH | CH | CH | Cl | | 1.63 | 289 | B | |
| P1.6 | CH | CH | CH | F | | 1.11 | 289 | B | |
| P1.7 | CH | CH | CH | F | | 1.28 | 344.6 M+CH3CN | B | |
| P1.8 | CH | CH | CH | F | | | | | 0.26 |

In the following tests, a formulated solution of compound of formula I are screened for biological efficacy against untreated controls.

Biology Examples

B1: *Myzus Persicae* (Green Peach Aphid) (Mixed Population, Feeding/Residual Contact Activity, Preventive)

Sunflower leaf discs are placed on agar in a 24-well microtiter plate and sprayed with test solutions of 200 ppm. After drying, the leaf discs are infested with an aphid population of mixed ages. After an incubation period of 6 days, samples are checked for mortality and special effects (e.g. phytotoxicity). Compounds P1.1, P1.2 and P1.5 give at least 80% control of *Myzus persicae*.

B2: *Myzus Persicae* (Green Peach Aphid) (Mixed Population, Systemic/Feeding Activity, Curative)

Roots of pea seedlings, infested with an aphid population of mixed ages, are placed directly in the test solutions of 24 ppm. 6 days after introduction, samples are checked for mortality and special effects on the plant.

Compounds P1.1, P1.2, P1.5 and P1.6 give at least 80% control of *Myzus persicae*.

B3: *Myzus Persicae* (Green Peach Aphid) (Mixed Population, Sachet Test)

Each well of a 24-well microtiter plate is filled with 0.6 ml 30% sucrose solution, containing 12.5 ppm of the test compounds. For producing the sachets, the wells are covered with streched parafilm and infested with a mixed population of *Myzus persicae*. 6 days after the infestation, samples are checked for mortality (feeding activity).

Compounds P1.1 and P1.5 give at least 80% control of *Myzus persicae*.

The invention claimed is:

1. A compound of the formula I:

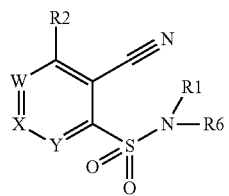

where
- W is N, NO, or C—$R^3$;
- X is N, NO or C—$R^4$;
- Y is N, NO, or C—$R^5$;
- $R^1$ and $R^6$ together with the adjacent nitrogen form a 5-membered ring containing, in addition to nitrogen and carbon ring members, a sulfur atom or a group selected from SO and $SO_2$,
- $R^2$ is H, halogen, cyano, C1-C6-alkyl, C1-C6-haloalkyl, C1-C6-alkoxy, C1-C6-haloalkoxy, C1-C6-alkylthio, C1-C6-alkylsulfinyl, C1-C6-alkylsulfonyl, C1-C6-haloalkylthio, C1-C6-haloalkylsulfinyl, C1-C6-haloalkylsulfonyl, C2-C6-alkenyl, C2-C6-alkynyl, C2-C6-haloalkenyl, C2-C6-haloalkynyl, amino, (C1-C6-alkyl)amino, di(C1-C6-alkyl)amino, aminosulfonyl, aminosulfinyl, aminosulfenyl, or $R^9C$(=O); provided that the C1-C6-alkyl, C1-C6-haloalkyl, C1-C6-alkoxy, C1-C6-haloalkoxy, C1-C6-alkylthio, C1-C6-alkylsulfinyl, C1-C6-alkylsulfonyl, C1-C6-haloalkylthio, C1-C6-haloalkylsulfinyl, C1-C6-haloalkylsulfonyl, C2-C6-alkenyl, C2-C6-alkynyl, C2-C6-haloalkenyl, C2-C6-haloalkynyl, (C1-C6-alkyl)amino, di(C1-C6-alkyl) amino radicals may be unsubstituted, or may carry 1, 2 or 3 radicals, independently of one another, each selected from the group consisting of cyano, nitro, amino, OH, C1-C6-alkyl, C1-C6-haloalkyl, C1-C6-alkoxy, C1-C6-alkylthio, C1-C6-alkylsulfinyl, C1-C6-alkylsulfonyl, C1-C6-haloalkoxy, C1-C6-haloalkylthio, (C1-C6-alkoxy)carbonyl, (C1-C6-alkyl)amino, di(C1-C6-alkyl)amino, C3-C8-cycloalkyl and partially or fully unsaturated ring system;
- $R^3$, $R^4$ and $R^5$, independently of each other, are H, halogen, cyano, azido, nitro, C1-C6-alkyl, C3-C8-cycloalkyl, C1-C6-haloalkyl, C1-C6-alkoxy, C1-C6-haloalkoxy, C1-C6-alkylthio, C1-C6-alkylsulfinyl, C1-C6-alkylsulfonyl, C1-C6-haloalkylthio, C2-C6-alkenyl, C2-C6-alkynyl, C2-C6-haloalkenyl, C2-C6-haloalkynyl, amino, (C1-C6-alkyl)amino, di(C1-C6-alkyl)amino, aminosulfonyl, aminosulfinyl, aminosulfenyl, $R^9C$(=O), aryl or heteroaryl, which heteroaryl may contain 1, 2 or 3 heteroatoms as ring members, independently of one another, selected from the group consisting of nitrogen, oxygen and sulfur and said aryl or heteroaryl may carry 1, 2 or 3 substituents, independently of one another, selected from the group consisting of halogen, C1-C6-alkyl, C1-C6-haloalkyl, C1-C6-alkoxy and C1-C6-haloalkoxy;
- each $R^9$ independently is selected from the group consisting of hydrogen, hydroxy, C1-C6-alkoxy, amino, (C1-C6-alkyl)amino, di(C1-C6-alkyl)amino, aryl, aryl-C1-C6-alkyl and C1-C6-alkyl,
- a 5- to 6-membered heteroaryl ring, wherein the heteroaryl ring contains as ring members 1, 2 or 3 heteroatoms or heteroatom groups, independently of one another, selected from the group consisting of nitrogen, oxygen, sulfur, SO, $SO_2$ and N—$R''$, wherein $R''$ is hydrogen or C1-C6-alkyl, and
- a 3- to 7-membered heterocyclyl ring, wherein the heterocyclic ring is saturated or partly unsaturated and contains 1, 2 or 3 heteroatoms or heteroatom groups, independently of one another, selected from the group consisting of nitrogen, oxygen, sulfur, group SO, $SO_2$ and N—$R^8$, wherein $R^8$ is hydrogen or C1-C6-alkyl, and wherein the carbon atoms of the heterocyclic rings may be unsubstituted or substituted by 1 or 2 radicals, independently of one another, selected from halogen and C1-C6-alkyl, and provided that the $R^9C$(=O) radical may be unsubstituted, or when $R^9$ is C1-C6-alkoxy, (C1-C6-alkyl)amino, di(C1-C6-alkyl)amino, aryl, aryl-C1-C6-alkyl and C1-C6-alkyl, the alkyl moiety may carry one or more halogen atoms;

or salts thereof.

2. The compound according to claim 1 wherein W, X and Y are each C—$R^3$, C—$R^4$ and C—$R^5$ respectively.

3. The compound according to claim 1 wherein W and Y are each CH, and X is CH or N.

4. The compound according to claim 1 wherein $R^2$ is halogen, C1-C6-alkyl, C1-C6-haloalkyl, C1-C6-alkoxy or C1-C6-haloalkoxy.

5. The compound according to claim 1 wherein W, X and Y are each CH, and $R^2$ is selected from halogen, C1-C6-alkyl, C1-C6-haloalkyl, C1-C6-alkoxy and C1-C6-haloalkoxy.

6. The compound according to claim 1 wherein W and Y are each CH, X is N, and $R^2$ is selected from halogen, C1-C6-alkyl, C1-C6-haloalkyl, Cl-C6-alkoxy and C1-C6-haloalkoxy.

7. The compound according to claim 1 wherein W and Y are each CH, X is N, and $R^2$ is C1-C6-alkoxy.

8. The compound according to claim 1 wherein $R^1$ and $R^6$ together with the adjacent nitrogen is thiazolidinyl.

9. A composition comprising the compound of claim 1 and one or more formulation auxiliaries.

10. A composition comprising the compound of claim 1, and one or more active ingredients, and optionally one or more formulation auxiliaries.

11. A method for controlling a pest in crop protection or for protecting a seed, a plant, parts of a plant or plant organs against pest damage, said method comprising applying a compound of claim 1 or a composition thereof to the pest, to the plant, to the seed, to the part of a plant or plant organ or the environment of each thereof.

12. A seed comprising a compound of claim 1.

13. A method for controlling a pest, said method comprising applying a compound of claim 1 to (i) the pest, (ii) material for protection against the pest, or (iii) an environment thereof.

14. The method according to claim 13 wherein the material is selected from a raw material, wood, textile, floor covering and building material.

15. The method according to claim 13 wherein the pest is controlled against damaging stored goods.

16. The method according to claim 13 wherein the pest is controlled for the protection of humans, domestic animals or productive livestock.

* * * * *